(12) United States Patent
Shen et al.

(10) Patent No.: US 8,822,491 B2
(45) Date of Patent: Sep. 2, 2014

(54) METHODS AND COMPOSITIONS FOR TREATING β-THALASSEMIA AND SICKLE CELL DISEASE

(75) Inventors: Che-kun James Shen, Taipei (TW); Yu-Chi Chou, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 13/984,687

(22) PCT Filed: Jan. 3, 2012

(86) PCT No.: PCT/US2012/020059
§ 371 (c)(1),
(2), (4) Date: Nov. 4, 2013

(87) PCT Pub. No.: WO2012/112232
PCT Pub. Date: Aug. 23, 2012

(65) Prior Publication Data
US 2014/0088133 A1 Mar. 27, 2014

Related U.S. Application Data

(60) Provisional application No. 61/444,436, filed on Feb. 18, 2011.

(51) Int. Cl.
*A61K 31/4745* (2006.01)
*A61K 31/4738* (2006.01)

(52) U.S. Cl.
USPC .......................................... 514/283; 514/280

(58) Field of Classification Search
USPC ................................. 514/283, 280
See application file for complete search history.

(56) References Cited

U.S. PATENT DOCUMENTS

2008/0234342 A1 9/2008 Granger et al.
2010/0272660 A1 10/2010 Malle

FOREIGN PATENT DOCUMENTS

EP 0 604 181 A1 * 6/1994 ........... C07D 471/06

OTHER PUBLICATIONS

Tokumitsu et al., STO-609, a specific inhibitor of the Ca(2+)/calmodulin-dependent protein kinase kinase. J Biol Chem. May 3, 2002;277(18):15813-8. Epub Feb. 26, 2002. Erratum in: J Biol Chem. Feb. 7, 2003;278(6):4368.

* cited by examiner

*Primary Examiner* — Charanjit Aulakh
(74) *Attorney, Agent, or Firm* — Wolf, Greenfield & Sacks, P.C.

(57) ABSTRACT

The present invention provides compounds (such as compounds of formula I-a) that induce γ globin expression and pharmaceutical compositions thereof. Such compounds may have beneficial therapeutic effects. Compounds and compositions described herein may be used to treat hemoglobinopathies such as β-thalassemia and sickle cell anemia.

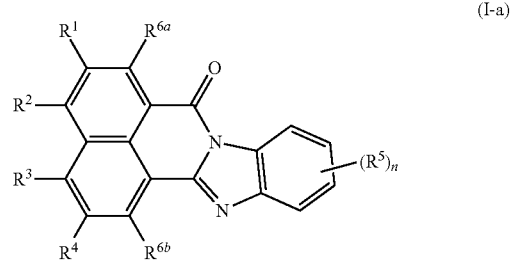

(I-a)

20 Claims, 11 Drawing Sheets

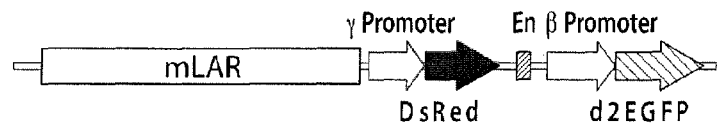

Fig. 2A

| Experimental Procedures | Description |
| --- | --- |
| Step 1 Chemicals Treatment | Inoculate 5 X 10⁴ MEL (Reporter) cells with 10 µM of pharmaceuticals in for 3 days |
| Step 2 Florescence Detection | Primary screening by Wallac VICTOR3™ Multilabel plate reader DsRed (Ex550/9, Em620) |
| Step 3 Microscope Observation (Digital Image Detection) | Secondary screening by observation of the DsRed signal in MEL cells with florescence microscope (or ArrayScan) |
| Step 4 Q-PCR Validation | Validation of the endogenous embryonic/fetal globin chains expression by RT-qPCR (≥ 10 fold increase) |

Fig. 2B

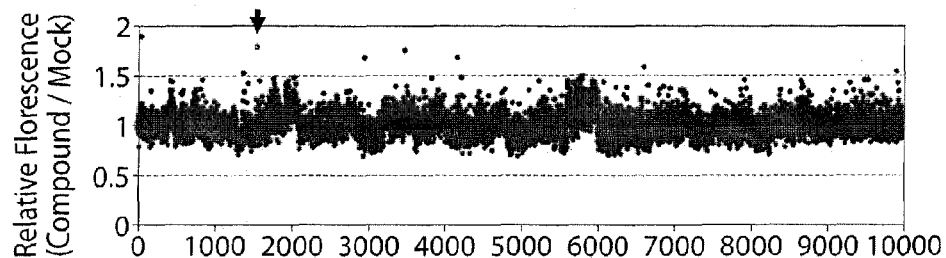

Fig. 2C

Compound A - 8-(3-Carboxy-7-oxo-7H-benzo[de]benzo[4,5]imidazo[2,1-a]isoquinolin-4-yl)-naphthalene-1,4,5-tricarboxylic acid
Compound B - Benzo[de]benzo[4,5]imidazo[2,1-a]isoquinolin-7-one
Compound C - 3-Chloro-benzo[de]benzo[4,5]imidazo[2,1-a]isoquinolin-7-one Compound D - 4-Nitro-benzo[de]benzo[4,5]imidazo[2,1-a]isoquinolin-7-one
Compound E - 4-Methylamino-benzo[de]benzo[4,5]imidazo[2,1-a]isoquinolin-7-one
Compound F - 7-Oxo-7H-benzo[de]benzo[4,5]imidazo[2,1-a]isoquinoline-3,4-dicarboxylic acid

|  | ε-globin (copies/μg) | γ-globin (copies/μg) | δ-globin (copies/μg) | β-globin (copies/μg) |
|---|---|---|---|---|
| Mock | $8.8 \times 10^6$ (0.1%) | $5.9 \times 10^8$ (8.0%) | $3.5 \times 10^8$ (4.7%) | $6.5 \times 10^9$ (87.2%) |
| HU | $47.9 \times 10^6$ (0.2%) | $11.1 \times 10^8$ (9.9%) | $7.6 \times 10^8$ (6.8%) | $9.3 \times 10^9$ (83.1%) |
| NaB | $17.6 \times 10^6$ (0.3%) | $7.4 \times 10^8$ (12.8%) | $1.8 \times 10^8$ (3.2%) | $4.8 \times 10^9$ (83.8%) |
| Compound A | $37.1 \times 10^6$ (0.6%) | $16.0 \times 10^8$ (19.6%) | $3.9 \times 10^8$ (4.7%) | $6.1 \times 10^9$ (75.2%) |
| Compound B | $54.7 \times 10^6$ (0.3%) | $17.5 \times 10^8$ (10.7%) | $12.4 \times 10^8$ (7.6%) | $13.4 \times 10^9$ (81.4%) |
| Compound C | $25.5 \times 10^6$ (0.3%) | $15.2 \times 10^8$ (15.6%) | $7.5 \times 10^8$ (7.6%) | $7.5 \times 10^9$ (76.5%) |
| Compound F | $68.1 \times 10^6$ (1.0%) | $11.0 \times 10^8$ (15.8%) | $6.6 \times 10^8$ (9.5%) | $5.2 \times 10^9$ (73.8%) |

Fig. 9

| Compound | IC50 (μM) [a] | EC(μM) [b] | IC50 / EC | γ-globin Induction Fold (IC50) |
|---|---|---|---|---|
| A | 0.17 | 0.12 | 1.41 | 2.71 |
| B | 21.82 | 2.26 | 9.65 | 2.97 |
| C | 75.19 | 9.31 | 8.07 | 2.58 |
| D | 3.61 | 1.93 | 1.87 | 2.19 |
| E | 135 | 25.83 | 5.23 | 3.42 |
| F | 103.02 | 75.86 | 1.36 | 1.87 |
| Butyric Acid | 221.556 | NA | NA | 1.25 |
| Hydroxyurea | 146.51 | 146.51 | 1 | 1.88 | a. IC50 values are the concentrations of the individual compounds at which the cell proliferation rates are reduced by 50%.

b. EC values are defined as the concentrations of compounds that induce the γ globin gene expression by 1.88 folds, the fold of γ globin gene induction by hydroxyurea at IC50

Fig. 10

```
SEQUENCE LISTING

<160> NUMBER OF SEQ ID NOS: 3

<210> SEQ ID NO 1
<211> LENGTH: 8003
<212> TYPE: DNA
<213> ORGANISM: Mus musculus

<400> SEQUENCE: 1
tcgactctag aggatcaatt cgagctcttg gggacccag tacacaagag gggacgcagg      60
gtatatgtag acatctcatt cttttctta gtgtgagaat aagaatagcc atgacctgag     120
tttatagaca atgagcctt ttctctctcc cactcagcag ctatgagatg gcttgccctg     180
cctctctact aggctgactc actccaaggc ccagcaatgg gcagggctct gtcagggctt    240
tgatagcact atctgcagag ccagggccga gaaggggtgg actccagaga ctctccctcc    300
cattcccgag cagggtttgc ttatttatgc atttaaatga tatatttatt ttaaaagaaa    360
taacaggaga ctgcccagcc ctggctgtga catggaaact atgtagaata ttttgggttc    420
catttttttt tccttctttc agttagagga aaaggggctc actgcacata cactagacag    480
aaagtcagga gctttgaatc caagcctgat catttccatg tcatactgag aaagtcccca    540
cccttctctg agcctcagtt tctctttta taagtaggag tctggagtaa atgatttcca    600
atggctctca tttcaataca aaatttccgt ttattaaatg catgagcttc tgttactcca    660
agactgagaa ggaaattgaa cctgagactc attgactggc aagatgtccc cagaggctct    720
cattcagcaa taaaattctc accttcaccc aggcccactg agtgtcagat ttgcatgcac    780
tagttcacgt gtgtaaaaag gaggatgctt cttttccttg tattctcaca tacctttagg    840
aaagaactta gcacccttcc cacacagcca tcccaataac tcatttcagt gactcaaccc    900
ttgactttat aaaagtcttg ggcagtatag agcagagatt aagagtacag atgctggagc    960
cagaccacct gagtgattag tgactcagtt tctcttagta attgtatgac tcagtttctt   1020
catctgtaaa atggagggtt ttttaattag tttgttttg agaaagggtc tcactctgtc    1080
acccaaatgg gagtgtagtg gcaaaatctc ggctcactgc aacttgcact tcccaggctc    1140
aagcggtcct cccacctcaa catcctgagt agctggaacc acaggtacac accaccatac   1200
ctcgctaatt ttttgtattt ttggtagaga tggggtttca catgttacac aggatggtct    1260
cagactccgg agctcagaag agtcaagcat ttgcctaagg tcggacatgt cagaggcagt    1320
gccagaccta tgtgagactc tgcagctact gctcatgggc cctgtgctgc actgatgagg   1380
aggatcagat ggatggggca atgaagcaaa ggaatcattc tgtggataaa ggagacagcc   1440
```

```
atgaagaagt ctatgactgt aaatttggga gcaggagtct ctaaggactt ggatttcaag    1500
gaattttgac tcagcaaaca caagaccctc acggtgactt tgcgagctgg tgtgccagat    1560
gtgtctatca gaggttccag ggagggtggg gtggggtcag ggctggccac cagctatcag    1620
ggcccagatg ggttataggc tggcaggctc agataggtgg ttaggtcagg ttggtggtgc    1680
tgggtggagt ccatgactcc caggagccag gagagataga ccatgagtag agggcagaca    1740
tgggaaaggt gggggaggca cagcatagca gcattttttca ttctactact acatgggact    1800
gctcccctat accccccagct aggggcaagt gccttgactc ctatgttttc aggatcatca    1860
tctataaagt aagagtaata attgtgtcta tctcataggg ttattatgag atcaaagga    1920 gatgcacact ctctggacca gtggcctaac agttcaggac agagctatgg cttcctatg    1980 tatgggtcag tggtctcaat gtagcaggca agttccagaa gatagcatca accactgtta    2040
gagatatact gccagtctca gagcctgatg ttaatttagc aatgggctgg accctcctc    2100 cagtagaacc ttctaaccag gatccagtgg ggcctctaag actaagtcac tctgtctcac    2160
tgtgtcttag ccagttcctt acagcttgcc ctgatgggag atagagaatg gtatcctcc    2220 aacaaaaaaa taaattttca tttctcaagg tccaacttat gttttcttaa tttttaaaaa    2280
aatcttgacc attctccact ctctaaaata atccacagtg agagaaacat tcttttcccc    2340
catcccataa atacctctat taaatatgga aaatctgggc atggtgtctc acacctgtaa    2400
tcccagcact ttgggaggct gaggtgggtg gactgcttgg agctcaggag ttcaagacca    2460
tcttggacaa catggtgata ccctgcctct acaaaaagta caaaaattag cctggcatgg    2520
tggtgtgcac ctgtaatccc agctattagg gtggctgagg caggagaatt gcttgaaccc    2580
gggaggcgga ggttgcagtg agctgagatc gtgccactgc actccagcct ggggacaga    2640 gcacattata attaactgtt attttttact tggactcttg tggggaataa gatacatgtt    2700
ttattcttat ttatgattca agcactgaaa atagtgttta gcatccagca ggtgcttcaa    2760
aaccatttgc tgaatgatta ctatactttt tacaagctca gctccctcta tcccttccag    2820
catcctcatc tctgattaaa taagcttcag ttttttcctta gttcctgtta catttctgtg    2880
tgtctccatt agtgacctcc catagtccaa gcatgagcag ttctggccag gcccctgtcg    2940
gggtcagtgc cccacccccg ccttctggtt ctgtgtaacc ttctaagcaa accttctggc    3000
tcaagcacag caatgctgag tcatgatgag tcatgctgag gcttagggtg tgtgcccaga    3060
tgttctcagc ctagagtgat gactcctatc tgggtcccca gcaggatgct tacagggcag    3120
atggcaaaaa aaaggagaag ctgaccacct gactaaaact ccacctcaaa cggcatcata    3180
aagaaaatgg atgcctgaga cagaatgtga catattctag aatatattat ttcctgaata    3240
tatatatata tatatataca catatacgta tatatatata tatatatata tttgttgtta    3300
tcaattgcca tagaatgatt agttattgtg aatcaaatat ttatcttgca ggtggcctct    3360
atacctagaa gcggcagaat caggctttat taatacatgt gtatagattt ttaggatcta    3420
tacacatgta ttaatatgaa acaaggatat ggaagaggaa ggcatgaaaa caggaaaaga    3480
aaacaaacct tgtttgccat tttaaggcac ccctggacag ctaggtggca aaaggcctgt    3540
gctgttagag gacacatgct cacatacggg gtcagatcaa ttctgtctga ttgttctctg    3600
acttatctac catttttccct ccttaaagaa actgtggaac ttccttcagc tagaggggcc    3660
tggctcagaa gcctctggtc agcatccaag aaatacttga tgtcactttg gctaaaggta    3720
tgatgtgtag acaagctcca gagatggttt ctcatttcca tatccaccca cccagctttc    3780
```

```
caatttttaaa gccaattctg aggtagagac tgtgatgaac aaacaccttg acaaaattca    3840
acccaaagac tcactttgcc tagcttcaaa atccttactc tgacatatac tcacagccag    3900
aaattagcat gcactagagt gtgcatgagt gcaacacaca cacacaccaa ttccatattc    3960
tctgtcagaa atcctgttg gttttttcgtg aaaggatgtt ttcagaggct gaccccttgc    4020
cttcacctcc aatgctacca ctctggtcta agtcactgtc accaccacct aaattatagc    4080
tgttgactca taacaatctt cctgcttcta ccactgcccc actacaattt cttcccaata    4140
tactatccaa attagtcttt tcaaaatgta agtcatatat ggtcacctct ttgttcaaag    4200
tcttctgata gtttcctata tcatttataa taaaaccaaa tccttacaat tctctacaat    4260
agttgttcat gcatatatta tgtttattac agatacgcat atatatagct ctcatataaa    4320
taaatatata tatttatgtg tatgtgtgta gagtgttttt tcttacaact ctatgatgta    4380
ggtattatta gtgtcccaaa ttttataatt taggacttct atgatctcat cttttattct    4440 cccccttcacc gaatctcatc ctacattggc cttattgata ttccttgaaa attctaagca    4500
tcttacatct ttagggtatt tacatttgcc attcccctatg ccctaaatat ttaatcatag    4560
tttcatataa atgggttcct catcatctat gggtactctc tcaggtgtta actttatagt    4620
gaggactttc ctgccatact acttaaagta gcgatacccct ttcaccctgt cctaatcaca    4680
ctctggcctt catttcagtt tttttttttt ctccatagca cctaatctca ttggtatata    4740
acatgtttca tttgcttatt taatgtcaag ctctttccac tatcaagtcc atgaaaacag    4800
gaactttatt cctctattct gtttttgtgc tgtattctta gcaattttac aattttgaat    4860
gaaatgaatg agcagtcaaa cacatataca actataatta aaaggatgta tgctgacaca    4920
tccactgcta tgcacacaca aagaaatcag tggagtagag ctggaagcgc taagcctgca    4980
tagagctagt tagccctccg caggcagagc cttgatggga ttactgagtt ctagaattgg    5040
actcatttgt tttgtaggct gagatttgct cttgaaaact tgttctgacc aaaataaaag    5100
gctcaaaaga tgaatatcga aaccagggtg ttttttacac tggaatttat aactagagca    5160
ctcatgttta tgtaagcaat taattgtttc atcagtcagg taaaagtaaa gaaaaactgt    5220
gccaaggcag gtagcctaat gcaatatgcc actaaagtaa acattattcc ataggtgtca    5280
gatatggctt attcatccat cttcatggga aggatggcct tggcctggac atcagtgtta    5340
tgtgaggttc aaaacacctc taggctataa ggcaacagag ctccttttttt ttttttctgt    5400 gctttcctgg ctgtccaaat tctaatgat aagcatactt ctattcaatg agaatattct    5460
gtaagattat agttaagaat tgtgggagcc attccgtctc ttatagttaa atttgagctt    5520
cttttatgat cactgttttt ttaatatgct ttaagttctg gggtacatgt gccatggtgg    5580
tttgctgcac ccatcaaccc gtcatctaca ttaggtattt ctcctaatgc tatccttccc    5640 ctagccccc acccccaaca ggcccccagtg tgtgatgttc ccctccctgt gtccatggat    5700 cactggttttt tttttttttt tttttttttt tttttaaagtc tcagttaaat ttttggaatg    5760
taatttattt tcctggtatc ctaggacctg caagttatcg ggtcacttta gccctcacgt    5820
tttgatgata atcacatatt tgtaaacaca acacacacac acacacacac acacatatat    5880
atatataaaa catatatata cataaacaca cataacatat ttatcgggca tttctgagca    5940
actaactcat gcaggactct caaacactaa cctatagcct tttctatgta tctacttgtg    6000
tagaaaccaa gcgtggggac tgagaaggca atagcaggag cattctgact ctcactgcct    6060
ttggctaggt ccctccctca tcacagctca gcatagtccg agctcttatc tatatccaca    6120
cacagtttct gacgctgccc agctatcacc atcccaagtc taaagaaaaa aataatgggt    6180
```

```
ttgcccatct ctgttgatta gaaaacaaaa caaaataaaa taagcccta agctcccaga      6240 aaacatgact aaaccagcaa gaagaagaaa atacaatagg tatatgagga gactggtgac      6300
actagtgtct gaatgaggct tgagtacaga aaagaggctc tagcagcata gtggtttaga      6360
ggagatgttt ctttccttca cagatgcctt agcctcaata agcttgcggt tgtggaagtt      6420
tactttcaga acaaactcct gtggggctag aattattgat ggctaaaaga agcccggggg      6480
agggaaaaat cattcagcat cctcacccctt agtgacacaa acagagggg gcctggtttt       6540 ccatatttcc tcatgatgga tgatctcgtt aatgaaggtg gtctgacgag atcattgctt      6600
cttccattta agccttgctc acttgccaat cctcagtttt aaccttctcc agagaaatac      6660
acatttttta ttcaggaaac atactatgtt atagtttcaa tactaaataa tcaaagtact      6720
gaagatagca tgcataggca agaaaaagtc cttagcttta tgttgctgtt gtttcagaat      6780
ttaaaaaaga tcaccaagtc aaggacttct cagttctagc actagaggtg gaatcttagc      6840
atataatcag aggttttttca aaatttctag acatgagatt caaagccctg cacttaaaat      6900
agtctcattt gaattaactc tttatataaa ttgaaagcac attctgaact acttcagagt      6960
attgttttat ttctatgttc ttagttcata aatacattag gcaatgcaat ttaattaaaa      7020
aaacccaaga atttcttaga attttaatca tgaaaataaa tgaaggcatc tttacttact      7080
caaggtccca aaaggtcaaa gaaccagga agtaaagct atatttcagc ggaaaatggg       7140
atatttatga gttttctaag ttgacagact caagttttaa ccttcagtgc ccatgatgta      7200
ggaaagtgtg gcataactgg ctgattctgg ctttctactc cttttttccca ttaaagatcc      7260 ctcctgctta attaacattc acaagtaact ctggttgtac tttaggcaca gtggctcccg      7320
aggtcagtca cacaatagga tgtctgtgct ccaagttgcc agagagagag attactcttg      7380
agaatgagcc tcagccctgg ctcaaactca cctgcaaact tcgtgagaga tgaggcagag      7440
gtacactacg aaagcaacag ttagaagcta aatgatgaga acacatggac tcatagaggg      7500
aaacaacgca tactggggcc tatcagaggg tggagggtga gagaaggaga ggatcaggaa      7560
aaatcactaa tggatgctaa gcgtaatacc tgagtgatga gatcatctat acaacaaacc      7620
cccttgacat tcatttatct atgtaacaaa cctgcacatc ctgtacacgt accccctgaac      7680 ttaaaataaa agttgaaaac aagaaagcaa cagtttgaac acttgttatg gtctattctc      7740
tcattcttta caattacact agaaaatagc cacaggctcc tgcaaggcag ccacagaatt      7800
tatgacttgt gatgatctaa tgctttcata aagaagcaaa tataataaat actataccac      7860
aaatgtaatg tttgatgtct gataatgata tttcagtgta attaaactta gcactcctat      7920
gtatattatt tgatgcaata aaaacatatt ttttttagca cttacagtct gccaaactgg      7980
cctgtgacac aaaaaaagtt tag                                              8003

<210> SEQ ID NO 2
<211> LENGTH: 1377
<212> TYPE: DNA
<213> ORGANISM: Homo sapiens

<400> SEQUENCE: 2
tacacaggat catgaaggat gaaagaactt caccaatatt ataataattt caatcaacct       60
gatagcttag gggataaact aatttgaaga tacagcttgc ctccgataag ccagaattcc      120
agagcttctg gcattataat ctagcaaggt tagagatcat ggatcacttt cagagaaaaa      180
caaaaacaaa ctaaccaaaa gcaaaacaga accaaaaaac caccataaat acttcctacc      240
```

-continued

```
ctgttaatgg tccaatatgt cagaaacagc gctgtgttag aaataaagct gtctaaagta    300
cactaatatt cgagttataa tagtgtgtgg actattagtc aataaaaaca acccttgcct    360
ctttagagtt gttttccatg tacacgcaca tcttatgtct tagagtaaga ttccctgaga    420
agtgaaccta gcatttatac aagataatta attctaatcc acagtacctg ccaaagaaca    480
ttctaccatc atctttactg agcatagaag gctacgccaa aaccctgggt catcagccag    540
cacacacact tatccagtgg taaatacaca tcatctggtg tatacataca tacctgaata    600
tggaatcaaa tattttttcta agatgaaaca gtcatgattt atttcaaata ggtacggata    660
agtagatatt gaggtaagca ttaggtctta tattatgtaa cactaatcta ttactgcgct    720
gaaactgtgg ctttatagaa attgttttca ctgcactatt gagaaattaa gagataatgg    780
caaaagtcac aaagagtata ttcaaaaaga agtatagcac ttttcctta gaaaccactg     840 ctaactgaaa gagactaaga tttgtcccgt caaaaatcct ggacctatgc ctaaaacaca    900
tttcacaatc cctgaacttt tcaaaaattg gtacatgctt tagctttaaa ctacaggcct    960
cactggagct agagacaaga aggtaaaaaa cggctgacaa agaagtcct ggtatcctct    1020 atgatgggag aaggaaacta gctaaaggga agaataaatt agagaaaaac tggaatgact  1080
gaatcggaac aaggcaaagg ctataaaaaa aattaagcag cagtatcctc ttgggggccc   1140
cttccccaca ctatctcaat gcaaatatct gtctgaaacg gtccctggct aaactccacc  1200
catgggttgg ccagccttgc cttgaccaat agccttgaca aggcaaactt gaccaatagt   1260
cttagagtat ccagtgaggc caggggccgg cggctggcta gggatgaaga ataaaaggaa  1320
gcacccttca gcagttccac acactcgctt ctggaacgtc tgaggttatc aataagc     1377
```

<210> SEQ ID NO 3
<211> LENGTH: 1622
<212> TYPE: DNA
<213> ORGANISM: Homo sapiens

<400> SEQUENCE: 3

```
gtcgactcta gaggatctct atttatttag caataataga gaaagcattt aagagaataa     60
agcaatggaa ataagaaatt tgtaaatttc cttctgataa ctagaaatag aggatccagt   120
ttcttttggt taacctaaat tttatttcat tttattgttt tatttttattt tatttttattt    180 tattttgtgt aatcgtagtt tcagagtgtt agagctgaaa ggaagaagta ggagaaacat    240
gcaaagtaaa agtataacac tttccttact aaaccgactg ggtttccagg taggggcagg   300
attcaggatg actgacaggg cccttaggga acactgagac cctacgctga cctcataaat    360
gcttgctacc tttgctgttt taattacatc ttttaatagc aggaagcaga actctgcact   420
tcaaagtttt ttcctcacct gaggagttaa tttagtacaa ggggaaaaag tacaggggga    480
tgggagaaag gcgatcacgt tgggaagcta tagagaaaga agagtaaatt ttagtaaagg   540
aggtttaaac aaacaaaata taagagaaa taggaacttg aatcaaggaa atgattttaa    600
aacgcagtat tcttagtgga ctagaggaaa aaaataatct gagccaagta gaagaccttt   660
tcccctccta cccctacttt ctaagtcaca gaggcttttt gttccccccag acactcttgc   720 agattagtcc aggcagaaac agttagatgt ccccagttaa cctcctatttt gacaccactg    780 attaccccat tgatagtcac actttgggtt gtaagtgact ttttatttat ttgtattttt    840
gactgcatta agaggtctct agttttttat ctcttgtttc ccaaaaccta ataagtaact    900
aatgcacaga gcacattgat ttgtattttat tctatttta gacataattt attagcatgc    960
atgagcaaat taagaaaaac aacaacaaat gaatgcatat atatgtatat gtatgtgtgt   1020
```

```
atatatacac atatatatat atattttttt tcttttctta ccagaaggtt ttaatccaaa    1080
taaggagaag atatgcttag aactgaggta gagttttcat ccattctgtc ctgtaagtat    1140
tttgcatatt ctggagacgc aggaagagat ccatctacat atcccaaagc tgaattatgg    1200
tagacaaagc tcttccactt ttagtgcatc aatttcttat ttgtgtaata agaaaattgg    1260
gaaaacgatc ttcaatatgc ttaccaagct gtgattccaa atattacgta aatacacttg    1320
caaaggagga tgtttttagt agcaatttgt actgatggta tggggccaag agatatatct    1380
tagagggagg gctgagggtt tgaagtccaa ctcctaagcc agtgccagaa gagccaagga    1440
caggtacggc tgtcatcact tagacctcac cctgtggagc cacaccctag ggttggccaa    1500
tctactccca ggagcaggga gggcaggagc cagggctggg cataaaagtc agggcagagc    1560
catctattgc ttacatttgc ttctgacaca actgtgttca ctagcaacct caaacagaca    1620
cc                                                                    1622
```

METHODS AND COMPOSITIONS FOR TREATING β-THALASSEMIA AND SICKLE CELL DISEASE

CROSS-REFERENCE TO RELATED APPLICATIONS

The present application is a national stage filing under 35 U.S.C. §371 of International Application PCT/US2012/020059, filed Jan. 3, 2012, which claims the benefit under 35 U.S.C. §119(e) of U.S. Provisional Patent Application Ser. No. 61/444,436, filed Feb. 18, 2011, the entirety of which is incorporated herein by reference.

BACKGROUND OF THE INVENTION

The human hemoglobin molecule consists of a protein heterotetramer (two α-like globin chains and two β-like globin chains) and four non-protein heme groups. The α-like and β-like globin gene clusters are located on different chromosomes, and expression of the different globin genes within the two gene clusters are under temporal control during development. Genetic defects, such as deletions or mutations, inside these globin gene loci result in abnormal synthesis of hemoglobins and consequently lead to hemoglobinopathies.

β-thalassemia and sickle cell disease are the two most common hemoglobinopathies, which together affect approximately 4.5% of populations worldwide. β-thalassemia is the result of either a deletion or mutation within the β-like globin gene cluster, diminishing the synthesis of adult β globin chain. Severe deficiency or absence of the β globin chain leads to imbalanced expression of the adult α globin chain and the overloaded α globin chain in turn precipitates and damages the red cell membrane, ultimately inducing rapid apoptosis of the erythrocytes during early erythroblast development (also termed β-thalassemia major or Cooley's anemia). Individuals with β-thalassemia major become profoundly anemic within 6 to 9 months after birth, the time when the hemoglobin switch is completed from HbF (α2/β2) to HbA (α2/β2).

Sickle cell disease is caused by a point mutation at the sixth position of the β globin chain (from Glu to Val). Patients with sickle cell disease are characterized by the existence of sickle hemoglobin HbS (α2/β$^S$2). The mutated adult β globin chain promotes the polymerization of HbS at low oxygen condition, which distorts the red blood cells into the characteristic sickle shape. The illness of sickle cell disease is primarily caused by hemolysis, since the misshaped sickle cells are destroyed inside the spleen within 10-20 days. With high risk of early death, life expectancy of patients with the sickle cell disease is reported to be shortened to an average of 42-48 years. Impairing the generation of normal adult hemoglobin, both β-thalassemia major and sickle cell disease patients require regular blood transfusion to replenish functional HbA for survival. However, constant transfusions are accompanied by a high cost (exceeding 1 billion US dollars per year in the US alone) and a high risk of iron overloading which often leads to death.

In both β-thalassemia and sickle cell disease, the elevated expression of HbF has been reported to be helpful in improving the clinical symptoms of the underlying diseases. In β-thalassemia major patients, elevation of the fetal γ globin chain synthesis balances the excess α globin chains by formation of HbF, thus modulating the severe anemia in patients. Moreover, the increase of the γ globin chain can also prevent the formation of HbS, and the existence of HbF directly inhibits the polymerization of HbS in the sickle cell patients.

Thus, pharmacological induction of HbF in patients with hemoglobinopathies is a potentially useful therapeutic strategy. To date, several chemotherapeutic agents, such as trichostatin A (histone deacetylase inhibitor), apicidin (histone deacetylase inhibitor), 5'-aza-cytidine (DNA methyltransferase inhibitor), hydroxyurea (ribonucleotide reductase inhibitor), butyrate and other short-chain fatty acids, have been demonstrated to stimulate fetal hemoglobin production. However, most of these HbF inducers show variable efficacies from individual to individual, low specificity in globin gene induction, and high toxicity with irreversible apoptosis. Among these drugs, hydroxyurea is the first US FDA-approved medicine for the curing of hemoglobinopathies disease. Unfortunately, approximately 25% of the recipients are poor or non-responders to hydroxyurea treatment. Moreover, potential side effects of myelosuppression and reproductive toxicity exist, leading to therapeutic concerns for the usage of hydroxyurea in patients.

In view of this, compounds that induce expression of endogenous embryonic/fetal globin chains for the treatment of β-thalassemia major and sickle cell diseases are of great clinical interest.

SUMMARY OF THE INVENTION

The present invention provides compositions and methods for the treatment of β-thalassemia and sickle cell disease through induction of endogenous embryonic/fetal globin chains, including γ globin gene induction in erythrocytes. Methods of the invention include the administration of a pharmaceutical composition to a subject comprising a therapeutically effective amount of a compound of the invention effective to treat, delay or prevent the adverse effects of β-thalassemia or sickle cell disease. In certain embodiments, a therapeutically effective amount of a compound described herein is effective for inducing expression of embryonic/fetal globin chains.

In some embodiments, pharmaceutical compositions of compounds for the treatment of β-thalassemia or sickle cell disease through induction of endogenous embryonic/fetal globin chains are provided. Provided compositions comprise an effective amount of a compound as described herein, and a pharmaceutically acceptable excipient. In other embodiments, compounds are provided that have the property of inducing expression of endogenous embryonic/fetal globin chains in erythroid cells, which may be present in a mammalian host, or in culture as an in vitro model.

In one aspect, the present invention provides a pharmaceutical composition comprising a compound of Formula (I-a):

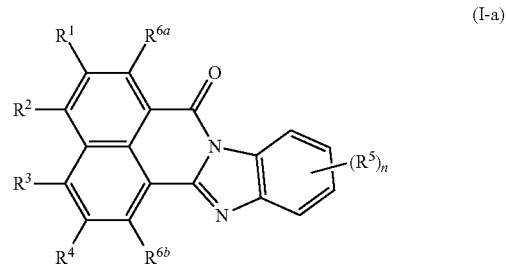

or a pharmaceutically acceptable salt, solvate, or hydrate thereof, wherein $R^1$, $R^2$, $R^3$, $R^4$, $R^5$, $R^{6a}$, $R^{6b}$, and n are as defined herein. In some embodiments, a pharmaceutical composition provided by the present invention is used to treat β-thalassemia or sickle cell anemia.

In another aspect, the present invention provides methods of inducing γ globin comprising contacting a cell with a compound or composition provided herein. In certain embodiments, the contacting step is performed in vitro. In other embodiments, the contacting step is performed in vivo. In certain embodiments, the present invention provides a method of treating β-thalassemia comprising administering an effective amount of a compound or composition provided herein to a patient in need thereof. In other embodiments, the present invention provides a method of treating sickle cell anemia comprising administering an effective amount of a compound or composition provided herein to a patient in need thereof.

In another aspect, the present invention provides methods of identifying inducers of γ globin expression. In certain embodiments, the method comprises incubating a test compound with an MEL cell containing human γ globin promoter, β globin promoter, and a dual fluorescence reporter plasmid, and determining fluorescence intensity compared to background signal. In certain embodiments, the present invention provides an MEL cell containing human γ globin promoter, β globin promoter, and a dual fluorescence reporter plasmid.

DEFINITIONS

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

As used throughout, "modulation" is meant to refer to an increase or a decrease in the indicated phenomenon (e.g., modulation of a biological activity refers to an increase in a biological activity or a decrease in a biological activity).

As used herein, the terms "treatment," "treating," and the like, refer to obtaining a desired pharmacologic and/or physiologic effect. The effect may be prophylactic in terms of completely or partially preventing a disease or condition, or symptom thereof, and/or may be therapeutic in terms of a partial or complete cure for a condition and/or adverse affect attributable to the condition. "Treatment," as used herein, covers any treatment of a disease or condition in a mammal, particularly in a human, and includes: (a) preventing the condition from occurring in a subject which may be predisposed to the condition but has not yet been diagnosed as having it; (b) inhibiting the development of the condition; and/or (c) relieving the condition, i.e., causing its regression.

An "effective amount" is an amount sufficient to effect beneficial or desired results. An effective amount can be administered in one or more administrations. An effective amount corresponds with the quantity required to provide a desired average local concentration of a particular biologic agent, in accordance with its known efficacy, for the intended period of therapy. A dose may be determined by those skilled in the art by conducting preliminary animal studies and generating a dose response curve, as is known in the art. Maximum concentration in the dose response curve would be determined by the solubility of the compound in the solution and by toxicity to the animal model, as known in the art.

The effective amount further corresponds with the quantity required to provide a desired average local concentration of the particular biologic agent, in accordance with its efficacy for the intended period of time. Due allowance can be made for losses due to circulatory fluctuation due to physical activity, for example, from ten to ninety percent loss allowance could be made depending upon the individual patient and their routines.

The terms "individual," "subject," "host," and "patient," used interchangeably herein, refer to a mammal, including, but not limited to, humans, murines, simians, felines, canines, equines, bovines, mammalian farm animals, mammalian sport animals, and mammalian pets. Human subjects are of particular interest.

As used herein, the terms "determining", "assessing", "assaying", "measuring" and "detecting" refer to both quantitative and qualitative determinations and as such, the term "determining" is used interchangeably herein with "assaying," "measuring," and the like. Where a quantitative determination is intended, the phrase "determining an amount" and the like is used. Where either a qualitative or quantitative determination is intended, the phrase "determining a level of proliferation" or "detecting proliferation" is used.

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in "Organic Chemistry," Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, the term "alkyl" is given its ordinary meaning in the art and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some cases, the alkyl group may be a lower alkyl group, i.e., an alkyl group having 1 to 10 carbon atoms (e.g., methyl, ethyl, propyl, butyl, pentyl, hexyl, heptyl, octyl, nonyl, or decyl). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, t-butyl, cyclobutyl, hexyl, and cyclochexyl.

The term "alkylene" as used herein refers to a bivalent alkyl group. An "alkylene" group is a polymethylene group, i.e., —$(CH_2)_z$—, wherein z is a positive integer, e.g., from 1 to 20, from 1 to 10, from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described herein for a substituted aliphatic group.

Generally, the suffix "-ene" is used to describe a bivalent group. Thus, any of the terms defined herein can be modified with the suffix "-ene" to describe a bivalent version of that moiety. For example, a bivalent carbocycle is "carbocyclylene", a bivalent aryl ring is "arylene", a bivalent benzene ring is "phenylene", a bivalent heterocycle is "heterocyclylene", a bivalent heteroaryl ring is "heteroarylene", a bivalent alkyl chain is "alkylene", a bivalent alkenyl chain is "alkenylene", a bivalent alkynyl chain is "alkynylene", a bivalent heteroalkyl chain is "heteroalkylene", a bivalent heteroalkenyl chain is "heteroalkenylene", a bivalent heteroalkynyl chain is "heteroalkynylene", and so forth.

The terms "alkenyl" and "alkynyl" are given their ordinary meaning in the art and refer to unsaturated aliphatic groups analogous in length and possible substitution to the alkyls described above, but that contain at least one double or triple bond respectively.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, t-butyl, n-pentyl, sec-pentyl, isopentyl, t-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargy 1), 1-propynyl and the like.

The term "cycloalkyl," as used herein, refers specifically to groups having three to ten, preferably three to seven carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or heterocyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl" is given its ordinary meaning in the art and refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, poly(ethylene glycol), and alkyl-substituted amino.

The terms "heteroalkenyl" and "heteroalkynyl" are given their ordinary meaning in the art and refer to unsaturated aliphatic groups analogous in length and possible substitution to the heteroalkyls described above, but that contain at least one double or triple bond respectively.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CHF$_2$; —CH$_2$F; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "aryl" is given its ordinary meaning in the art and refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. Substituents include, but are not limited to, any of the previously mentioned substitutents, i.e., the substituents recited for aliphatic moieties, or for other moieties as disclosed herein, resulting in the formation of a stable compound. In some cases, an aryl group is a stable mono- or polycyclic unsaturated moiety having preferably 3-14 carbon atoms, each of which may be substituted or unsubstituted. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups.

The terms "heteroaryl" is given its ordinary meaning in the art and refers to aryl groups comprising at least one heteroatom as a ring atom. A "heteroaryl" is a stable heterocyclic or polyheterocyclic unsaturated moiety having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In some cases, a heteroaryl is a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will also be appreciated that aryl and heteroaryl moieties, as defined herein may be attached via an alkyl or heteroalkyl moiety and thus also include -(alkyl)aryl, -(heteroalkyl)aryl, -(heteroalkyl)heteroaryl, and -(heteroalkyl)heteroaryl moieties. Thus, as used herein, the phrases "aryl or heteroaryl moieties" and "aryl, heteroaryl, -(alkyl)aryl, -(heteroalkyl)aryl, -(heteroalkyl)heteroaryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$F; —CHF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The term "heterocycle" is given its ordinary meaning in the art and refers to refer to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms.

The term "heterocycle" may include heteroaryl groups, saturated heterocycles (e.g., cycloheteroalkyl) groups, or combinations thereof. The heterocycle may be a saturated molecule, or may comprise one or more double bonds. In some cases, the heterocycle is a nitrogen heterocycle, wherein at least one ring comprises at least one nitrogen ring atom. The heterocycles may be fused to other rings to form a polycylic heterocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

The terms "halo" and "halogen" as used herein refer to an atom selected from fluorine, chlorine, bromine, and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino," as used herein, refers to a primary (—NH$_2$), secondary (—NHR$_x$), tertiary (—NR$_x$R$_y$), or quaternary (—N$^+$R$_x$R$_y$R$_z$) amine, where R$_x$, R$_y$ and R$_z$ are independently an aliphatic, alicyclic, heteroaliphatic, heterocyclic, aryl, or heteroaryl moiety, as defined herein. Examples of amino groups include, but are not limited to, methylamino, dimethylamino, ethylamino, diethylamino, methylethylamino, iso-propylamino, piperidino, trimethylamino, and propylamino.

The term "alkyne" is given its ordinary meaning in the art and refers to branched or unbranched unsaturated hydrocarbon groups containing at least one triple bond. Non-limiting examples of alkynes include acetylene, propyne, 1-butyne, 2-butyne, and the like. The alkyne group may be substituted and/or have one or more hydrogen atoms replaced with a functional group, such as a hydroxyl, halogen, alkoxy, and/or aryl group.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, t-butoxy, neopentoxy and n-hexoxy. Examples of thioalkyl include, but are not limited to, methylthio, ethylthio, propylthio, isopropylthio, n-butylthio, and the like.

The term "aryloxy" refers to the group, —O-aryl. The term "acyloxy" refers to the group, —O-acyl.

The term "alkoxyalkyl" refers to an alkyl group substituted with at least one alkoxy group (e.g., one, two, three, or more, alkoxy groups). For example, an alkoxyalkyl group may be —(C$_{1-6}$-alkyl)-O—(C$_{1-6}$-alkyl), optionally substituted. In some cases, the alkoxyalkyl group may be optionally substituted with another alkyoxyalkyl group (e.g., —(C$_{1-6}$-alkyl)-O—(C$_{1-6}$-alkyl)-O—(C$_{1-6}$-alkyl), optionally substituted.

It will be appreciated that the above groups and/or compounds, as described herein, may be optionally substituted with any number of substituents or functional moieties. That is, any of the above groups may be optionally substituted. As used herein, the term "substituted" is contemplated to include all permissible substituents of organic compounds, "permissible" being in the context of the chemical rules of valence known to those of ordinary skill in the art. In general, the term "substituted" whether preceeded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful for the formation of an imaging agent or an imaging agent precursor. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

Any of the compounds described herein may be in a variety of forms, such as, but not limited to, salts, solvates, hydrates, tautomers, and isomers.

The term "pharmaceutically acceptable salt" as used herein refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counter ions such as halide, hydroxide, carboxylate, sulfate, phosphate, nitrate, loweralkyl sulfonate and aryl sulfonate.

In certain embodiments, the compound is in the form of a hydrate or solvate. The term "hydrate" as used herein refers to a compound noncovalently associated with one or more molecules of water. Likewise, the term "solvate" refers to a compound non covalently associated with one or more molecules of an organic solvent.

In certain embodiments, the compound described herein may exist in various tautomeric forms. The term "tautomer" as used herein includes two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol; amide-to-imide; lactam-to-lactim; enamine-to-imine; and enamine-to-(a different) enamine tautomerizations.

In certain embodiments, the compounds described herein may exist in various isomeric forms. The term "isomer" as used herein includes any and all geometric isomers and stereoisomers (e.g., enantiomers, diastereomers, etc.). For example, "isomer" includes cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw Hill, N.Y., 1962); Wilen, S. H. *Tables of Resolving Agents and Optical Resolutions* p. 268 (E. L. Eliel, Ed., Univ. of Notre Dame Press, Notre Dame, Ind. 1972).

The present invention provides the endogenous embryonic/fetal globin chain inducers in a variety of formulations for therapeutic administration. In one aspect, the agents are formulated into pharmaceutical compositions by combination with appropriate, pharmaceutically acceptable carriers or diluents, and are formulated into preparations in solid, semisolid, liquid or gaseous forms, such as tablets, capsules, powders, granules, ointments, solutions, suppositories, injections, inhalants, gels, microspheres, and aerosols. As such, administration is achieved in various ways. In some formulations, the inducers are systemic after administration; in others, the inhibitor is localized by virtue of the formulation, such as the use of an implant that acts to retain the active dose at the site of implantation.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

It must be noted that as used herein and in the appended claims, the singular forms "a," "and," and "the" include plural referents unless the context clearly dictates otherwise. Thus, for example, reference to "a biomarker" includes a plurality of such biomarkers and reference to "the sample" includes reference to one or more samples and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Moreover any positively recited element of the disclosure provides basis for a negative limitation to exclude that element from the claims.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 9 shows absolute quantitative analysis of the level of the β-like globin mRNAs in primary erythroid cultures. The differentiated human primary erythroid cells were treated with compound A (0.2 µM), compound B (21.8 µM), compound C (75.2 µM), compound F (103 µM), hydroxyurea (HU; 146.5 µM) or sodium butyrate (NaB; 221.5 µM) at $IC_{50}$ for 3 days, and the levels of the mRNAs were analyzed by real time RT-PCR analysis. The copy number of each globin mRNA per µg of the total mRNA was estimated and shown. The relative proportions (%) of the individual globin chains among the total β-like globin mRNAs are indicated in the parentheses.

FIG. 10 shows a comparison of $IC_{50}$ and the γ globin gene induction abilities of the six heterocyclic compounds, sodium butyrate, and hydroxyurea. The induction folds of the γ globin gene expression were determined by real time RT-PCR analysis of mRNA from human primary erythroid cultures with and without treatment with the six heterocyclic compounds, butyratic acid, and hydroxyurea. $IC_{50}$ values are the concentrations of the individual compounds at which the cell proliferation rates are reduced by 50%. The effective concentration (EC) is defined as the concentration of compound(s) that induces the γ globin gene expression by 1.88-fold, the fold of the γ globin gene induction by hydroxyurea at its $IC_{50}$. The therapeutic window is calculated as the ratio of $IC_{50}$ to EC ($IC_{50}$/EC), which reflects the benefit of the heterocyclic compound in comparison to hydroxyurea.

DETAILED DESCRIPTION OF CERTAIN EMBODIMENTS OF THE INVENTION

Figure 1:
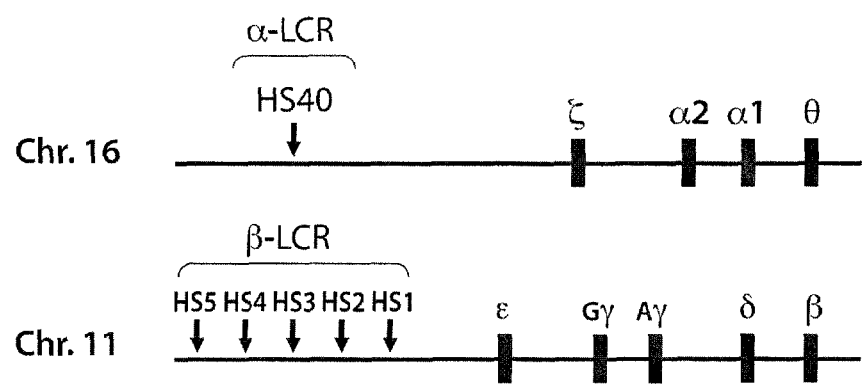
FIG. 1 shows physical maps of the human α-like and β-like globin gene clusters. The gene clusters of the human α-like and β-like globins, located on chromosomes 16 and 11, respectively, both extend over 50 kb of the genome. Each gene cluster consists of an upstream locus control region (LCR) and downstream paralogic globin genes. The expression of the individual globin genes in erythroid cells are under temporal control during development, known as the hemoglobin switch. The hemoglobin switch proceeds with reciprocal silencing of the embryonic/fetal globin genes and coordinate activation of the fetal/adult globin genes at each developmental stage, which is also accompanied with shifting of the erythropoiesis sites.

The present invention stems, in part, from the discovery that small molecules have been identified that can induce γ globin gene expression. The compounds identified herein are useful for treatment of β-thalassemia or sickle cell disease through induction of endogenous embryonic/fetal globin chains.

Compounds of interest are naphthoylenebenzimidazoles, e.g., compounds that include a naphthoylenebenzimidazole scaffold substituted with one or more substituents. The naphthoylenebenzimidazole scaffold of Formula (I) may be substituted at any position 1, 2, 3, 4, 5, 6, 7, 8, 9, and/or 10:

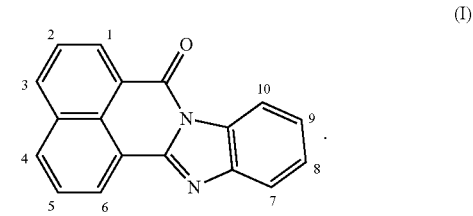 [SMILES: O=c1c2cccc3cccc(c32)c2nc3ccccc3n12]

(I)

In certain embodiments, positions 3 and 4 of the naphthoylenebenzimidazole scaffold are substituted.

In certain embodiments, a substituent may contribute to optical isomerism and/or stereo isomerism of a compound. Salts, solvates, hydrates, and prodrug forms of a compound are also of interest. All such forms are embraced by the present invention. Thus the compounds described herein include salts, solvates, hydrates, prodrug, and isomer forms thereof, including the pharmaceutically acceptable salts, solvates, hydrates, prodrugs, and isomers thereof. In certain embodiments, a compound may be a metabolized into a pharmaceutically active derivative.

In certain embodiments, the present invention employs a compound of Formula (I-a):

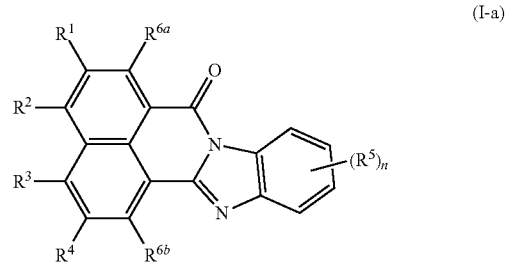

(I-a)

or a pharmaceutically acceptable salt, solvate, or hydrate thereof, wherein:

$R^1$, $R^2$, $R^3$, $R^4$, $R^{6a}$, and $R^{6b}$ are each independently selected from the group consisting of hydrogen, halogen, alkyl, alkenyl, alkynyl, heterocyclyl, aryl, —$OR^A$, —OC(O)$R^A$, —$SR^A$, —N($R^B$)$_2$, —N($R^A$)C(O)$R^A$, —C(O)N($R^B$)$_2$, —CN, —NO$_2$, —C(O)$R^A$, —C(O)O$R^A$, —S(O)$R^A$, —SO$_2R^A$, —SO$_2$N($R^B$)$_2$, and —NHSO$_2R^B$;

each instance of $R^5$ is independently selected from the group consisting of hydrogen, halogen, alkyl, alkenyl, alkynyl, heterocyclyl, aryl, —$OR^A$, —OC(O)$R^A$, —$SR^A$, —N($R^B$)$_2$, —N($R^A$)C(O)$R^A$, —C(O)N($R^B$)$_2$, —CN, —NO$_2$, —C(O)$R^A$, —C(O)O$R^A$, —S(O)$R^A$, —SO$_2R^A$, —SO$_2$N($R^B$)$_2$, and —NHSO$_2R^B$;

each $R^A$ is independently selected from the group consisting of hydrogen, alkyl, alkenyl, alkynyl, heterocyclyl, and aryl;

each $R^B$ is independently selected from the group consisting of hydrogen, alkyl, alkenyl, alkynyl, heterocyclyl, and aryl, or two $R^B$ taken together with the intervening nitrogen form a heterocycle;

n is 0, 1, 2, 3, or 4.

In some embodiments, $R^{6a}$ and $R^{6b}$ are each hydrogen. In certain embodiments, the present invention employs a compound of Formula (II):

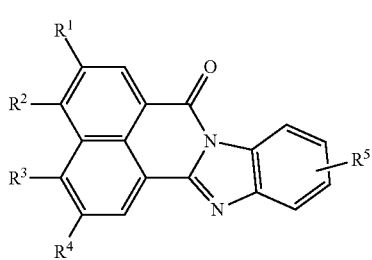

(II)

or a pharmaceutically acceptable salt, solvate, or hydrate thereof, wherein $R^1$, $R^2$, $R^3$, $R^4$ and $R^5$ are as described herein.

As described generally above, $R^1$ is hydrogen, halogen, alkyl, alkenyl, alkynyl, heterocyclyl, aryl, —$OR^A$, —OC(O)$R^A$, —$SR^A$, —N($R^B$)$_2$, —N($R^A$)C(O)$R^A$, —C(O)N($R^B$)$_2$, —CN, —NO$_2$, —C(O)$R^A$, —C(O)O$R^A$, —S(O)$R^A$, —SO$_2R^A$, —SO$_2$N($R^B$)$_2$, or —NHSO$_2R^B$. In certain embodiments, $R^1$ is selected from —H, —OH, —Cl, —Br, —F, $C_{1-6}$ alkyl, $C_{1-6}$ alkoxy, alkynyl, aryl, —NO$_2$, —N($R^B$)$_2$, —C(O)CH$_3$, —CO$_2$H, —C(O)O$R^A$, —C(O)N($R^B$)$_2$, —CN, heterocyclyl, —SO$_2$-alkyl, and —SO$_2$-aryl. In certain embodiments, $R^1$ is selected from —H, —OH, —Cl, —Br, —F, methyl, ethyl, methoxy, ethoxy, —C≡C-aryl, phenyl, naphthyl, —NO$_2$, —NH—$C_{1-6}$ alkyl, —C(O)CH$_3$, —CO$_2$H, —CO$_2$Et, —CONH-aryl, —CN, N-morpholinyl, —SO$_2$-alkyl, and —SO$_2$-aryl. In certain embodiments, $R^1$ is hydrogen. In some embodiments, $R^1$ is $C_{1-6}$ alkyl. In certain embodiments, $R^1$ is —C(O)O$R^A$. In certain embodiments, $R^1$ is —CO$_2$H. In certain embodiments, $R^1$ is —C(O)N($R^B$)$_2$ or —N($R^A$)C(O)$R^A$. In some embodiments, $R^1$ is halogen. In certain embodiments, $R^1$ is fluoro. In certain embodiments, $R^1$ is chloro. In some embodiments, $R^1$ is —N($R^B$)$_2$. In some embodiments, $R^1$ is —NH—$C_{1-6}$ alkyl. In certain embodiments, $R^1$ is —NHCH$_3$. In certain embodiments, $R^1$ is —NO$_2$. In certain embodiments, $R^1$ is optionally substituted naphthyl.

As described generally above, $R^2$ is hydrogen, halogen, alkyl, alkenyl, alkynyl, heterocyclyl, aryl, —$OR^A$, —OC(O)$R^A$, —$SR^A$, —N($R^B$)$_2$, —N($R^A$)C(O)$R^A$, —C(O)N($R^B$)$_2$, —CN, —NO$_2$, —C(O)$R^A$, —C(O)O$R^A$, —S(O)$R^A$, —SO$_2R^A$, —SO$_2$N($R^B$)$_2$, or —NHSO$_2R^B$. In certain embodiments, $R^2$ is selected from —H, —OH, —Cl, —Br, —F, $C_{1-6}$ alkyl, $C_{1-6}$ alkoxy, alkynyl, aryl, —NO$_2$, —N($R^B$)$_2$, —C(O)CH$_3$, —CO$_2$H, —C(O)O$R^A$, —C(O)N($R^B$)$_2$, —CN, heterocyclyl, —SO$_2$-alkyl, and —SO$_2$-aryl. In certain embodiments, $R^2$ is selected from —H, —OH, —Cl, —Br, —F, methyl, ethyl, methoxy, ethoxy, —C≡C-aryl, phenyl, naphthyl, —NO$_2$, —NH—$C_{1-6}$ alkyl, —C(O)CH$_3$, —CO$_2$H, —CO$_2$Et, —CONH-aryl, —CN, N-morpholinyl, —SO$_2$-alkyl, and —SO$_2$-aryl. In certain embodiments, $R^2$ is hydrogen. In some embodiments, $R^2$ is $C_{1-6}$ alkyl. In certain embodiments, $R^2$ is —C(O)O$R^A$. In certain embodiments, $R^2$ is —CO$_2$H. In certain embodiments, $R^2$ is —C(O)N($R^B$)$_2$ or —N($R^A$)C(O)$R^A$. In some embodiments, $R^2$ is halogen. In certain embodiments, $R^2$ is fluoro. In certain embodiments, $R^2$ is chloro. In some embodiments, $R^2$ is —N($R^B$)$_2$. In some embodiments, $R^2$ is —NH—$C_{1-6}$ alkyl. In certain embodiments, $R^2$ is —NHCH$_3$. In certain embodiments, $R^2$ is —NO$_2$. In some embodiments, $R^2$ is optionally substituted naphthyl.

As described generally above, $R^3$ is hydrogen, halogen, alkyl, alkenyl, alkynyl, heterocyclyl, aryl, —$OR^A$, —OC(O)$R^A$, —$SR^A$, —N($R^B$)$_2$, —N($R^A$)C(O)$R^A$, —C(O)N($R^B$)$_2$, —CN, —NO$_2$, —C(O)$R^A$, —C(O)O$R^A$, —S(O)$R^A$, —SO$_2R^A$, —SO$_2$N($R^B$)$_2$, or —NHSO$_2R^B$. In certain embodiments, $R^3$ is selected from —H, —OH, —Cl, —Br, —F, $C_{1-6}$ alkyl, $C_{1-6}$ alkoxy, alkynyl, aryl, —NO$_2$, —N($R^B$)$_2$, —C(O)CH$_3$, —CO$_2$H, —C(O)O$R^A$, —C(O)N($R^B$)$_2$, —CN, heterocyclyl, —SO$_2$-alkyl, and —SO$_2$-aryl. In certain embodiments, $R^3$ is selected from —H, —OH, —Cl, —Br, —F, methyl, ethyl, methoxy, ethoxy, —C≡C-aryl, phenyl, naphthyl, —NO$_2$, —NH—$C_{1-6}$ alkyl, —C(O)CH$_3$, —CO$_2$H, —CO$_2$Et, —CONH-aryl, —CN, N-morpholinyl, —SO$_2$-alkyl, and —SO$_2$-aryl. In certain embodiments, $R^3$ is hydrogen. In some embodiments, $R^3$ is $C_{1-6}$ alkyl. In certain embodiments, $R^3$ is —C(O)O$R^A$. In certain embodiments, $R^3$ is —CO$_2$H. In certain embodiments, $R^3$ is —C(O)N($R^B$)$_2$ or —N($R^A$)C(O)$R^A$. In certain embodiments, $R^3$ is halogen. In certain embodiments, $R^3$ is fluoro. In certain embodiments, $R^3$ is chloro. In some embodiments, $R^3$ is —N($R^B$)$_2$. In some embodiments, $R^3$ is —NH—$C_{1-6}$ alkyl. In certain embodiments, $R^3$ is —NHCH$_3$. In certain embodiments, $R^3$ is —NO$_2$. In certain embodiments, $R^3$ is optionally substituted naphthyl.

As described generally above, $R^4$ is hydrogen, halogen, alkyl, alkenyl, alkynyl, heterocyclyl, aryl, —$OR^A$, —OC(O)$R^A$, —$SR^A$, —N($R^B$)$_2$, —N($R^A$)C(O)$R^A$, —C(O)N($R^B$)$_2$, —CN, —NO$_2$, —C(O)$R^A$, —C(O)O$R^A$, —S(O)$R^A$, —SO$_2R^A$, —SO$_2$N($R^B$)$_2$, or —NHSO$_2R^B$. In certain embodiments, $R^4$ is selected from —H, —OH, —Cl, —Br, —F, $C_{1-6}$ alkyl, $C_{1-6}$ alkoxy, alkynyl, aryl, —NO$_2$, —N($R^B$)$_2$, —C(O)CH$_3$, —CO$_2$H, —C(O)O$R^A$, —C(O)N($R^B$)$_2$, —CN, heterocyclyl, —SO$_2$-alkyl, and —SO$_2$-aryl. In certain embodiments, $R^4$ is selected from —H, —OH, —Cl, —Br, —F, methyl, ethyl, methoxy, ethoxy, —C≡C-aryl, phenyl, naphthyl, —NO$_2$, —NH—$C_{1-6}$ alkyl, —C(O)CH$_3$, —CO$_2$H, —CO$_2$Et, —CONH-aryl, —CN, N-morpholinyl, —SO$_2$-alkyl, and —SO$_2$-aryl. In certain embodiments, $R^4$ is hydrogen. In certain embodiments, $R^4$ is $C_{1-6}$ alkyl. In certain embodiments, $R^4$ is —C(O)O$R^A$. In certain embodiments, $R^4$ is —CO$_2$H. In certain embodiments, $R^4$ is —C(O)N($R^B$)$_2$ or —N($R^A$)C(O)$R^A$. In some embodiments, $R^4$ is halogen. In certain embodiments, $R^4$ is fluoro. In certain embodiments, $R^4$ is chloro. In some embodiments, $R^4$ is —N($R^B$)$_2$. In some embodiments, $R^4$ is —NH—$C_{1-6}$ alkyl. In certain embodiments, R⁴ is —NHCH₃. In certain embodiments, R⁴ is —NO₂. In some embodiments, R⁴ is optionally substituted naphthyl.

As described generally above, R⁵ is hydrogen, halogen, alkyl, alkenyl, alkynyl, heterocyclyl, aryl, —OR^A, —OC(O)R^A, —SR^A, —N(R^B)₂, —N(R^A)C(O)R^A, —C(O)N(R^B)₂, —CN, —NO₂, —C(O)R^A, —C(O)OR^A, —S(O)R^A, —SO₂R^A, —SO₂N(R^B)₂, or —NHSO₂R^B. In certain embodiments, R⁵ is selected from —H, —OH, —Cl, —Br, —F, C₁₋₆ alkyl, C₁₋₆ alkoxy, alkynyl, aryl, —NO₂, —N(R^B)₂, —C(O)CH₃, —CO₂H, —C(O)OR^A, —C(O)N(R^B)₂, —CN, heterocyclyl, —SO₂-alkyl, and —SO₂-aryl. In certain embodiments, R⁵ is selected from —H, —OH, —Cl, —Br, —F, methyl, ethyl, methoxy, ethoxy, —C≡C-aryl, phenyl, naphthyl, —NO₂, —NH—C₁₋₆ alkyl, —C(O)CH₃, —CO₂H, —CO₂Et, —CONH-aryl, —CN, N-morpholinyl, —SO₂-alkyl, and —SO₂-aryl. In certain embodiments, R⁵ is hydrogen. In some embodiments, R⁵ is C₁₋₆ alkyl. In certain embodiments, R⁵ is —C(O)OR^A. In certain embodiments, R⁵ is —CO₂H. In certain embodiments, R⁵ is —C(O)N(R^B)₂ or —N(R^A)C(O)R^A. In some embodiments, R⁵ is halogen. In certain embodiments, R⁵ is fluoro. In certain embodiments, R⁵ is chloro. In some embodiments, R⁵ is —N(R^B)₂. In some embodiments, R⁵ is —NH—C₁₋₆ alkyl. In certain embodiments, R⁵ is —NHCH₃. In certain embodiments, R⁵ is —NO₂. In some embodiments, R⁵ is optionally substituted naphthyl.

In some embodiments, at least two of R¹, R², R³, and R⁴ are hydrogen. In certain embodiments, R¹ and R⁴ are hydrogen. In certain embodiments, R³ and R⁴ are hydrogen. In certain embodiments, R¹ and R² are hydrogen. In some embodiments, at least two of R¹, R², R³, and R⁴ are each hydrogen, and R⁵ is hydrogen.

In some embodiments, the compound is of Formula (III), (IV), or (V):

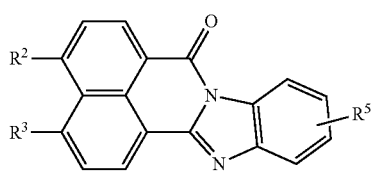

(III)

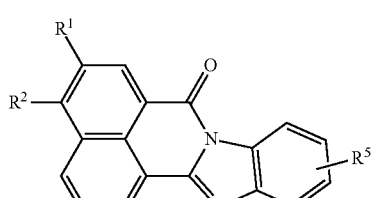

(IV)

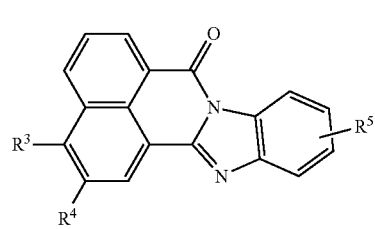

(V)

or a pharmaceutically acceptable salt, solvate, or hydrate thereof, wherein R¹, R², R³, R⁴, and R⁵ are as defined herein.

In some embodiments, R⁵ is hydrogen to give Formula (III-a), (IV-a), or (V-a):

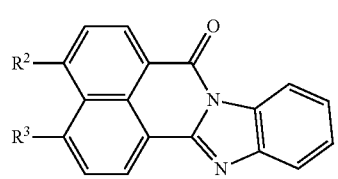

(III-a)

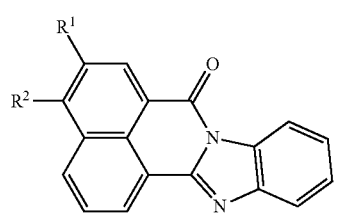

(IV-a)

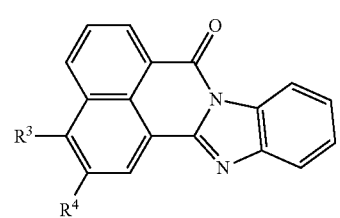

(V-a)

or a pharmaceutically acceptable salt, solvate, or hydrate thereof, wherein R¹, R², R³, and R⁴ are as defined herein.

In certain embodiments, one of R² or R³ is hydrogen to give Formula (III-b) or (III-c):

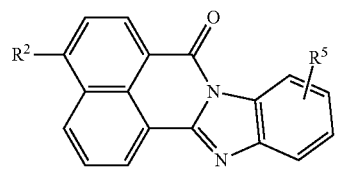

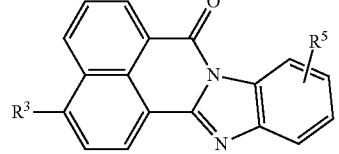

In some embodiments, one of R¹, R², R³, and R⁴ is of the following structure:

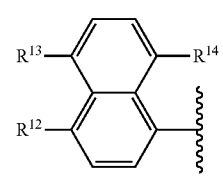

wherein R¹² and R¹³ are independently selected from hydrogen, —CO₂H, —C(O)OR^A, —C(O)N(R^B)₂, —OH, —NO₂, —CN, halogen, alkyl, aryl and heterocyclyl, or R¹² and R¹³ are taken together with their intervening atoms to form a carbocycle or heterocycle; and R¹⁴ is selected from hydrogen, —CO₂H, —C(O)OR^A, —C(O)N(R^B)₂, —OH, —NO$_2$, —CN, halogen, alkyl, aryl and heterocyclyl. In certain embodiments, R$^{12}$ and R$^{13}$ are taken together with their intervening atoms to form a carbocycle or heterocycle. In certain embodiments, R$^{12}$ and R$^{13}$ are taken together with their intervening atoms to form a heterocycle (e.g., a succinimide).

In certain embodiments, R$^{12}$ is —CO$_2$H. In certain embodiments, R$^{13}$ is —CO$_2$H. In certain embodiments, R$^{14}$ is —CO$_2$H.

In certain embodiments, R$^{12}$ and R$^{13}$ are each —CO$_2$H.

In certain embodiments, R$^{12}$, R$^{13}$, and R$^{14}$ are each —CO$_2$H.

In certain embodiments, one of R$^1$, R$^2$, R$^3$, and R$^4$ is of the following structure:

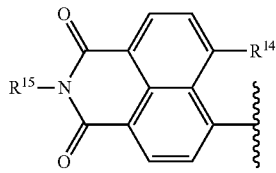

wherein R$^{14}$ is hydrogen, —CO$_2$H, —C(O)OR$^A$, —C(O)N(R$^B$)$_2$, —OH, —NO$_2$, —CN, halogen, alkyl, aryl and heterocyclyl; and R$^{15}$ is selected from hydrogen, acyl, alkyl, aryl, and heterocyclyl. In certain embodiments, R$^{14}$ is —CO$_2$H. In certain embodiments, R$^{14}$ is hydrogen. In certain embodiments, R$^{15}$ is hydrogen. In certain embodiments, R$^{15}$ is alkyl. In certain embodiments, R$^{15}$ is acyl.

In some embodiments, the compound is of the structure of Formula (VI) or (VII):

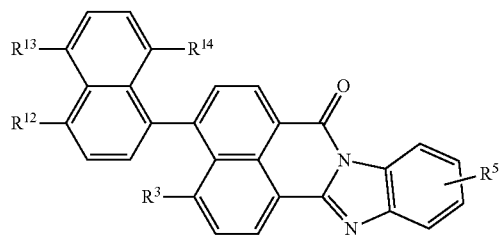

(VI)

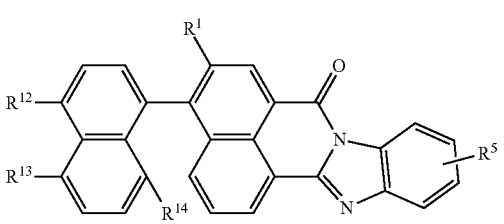

(VII)

or a pharmaceutically acceptable salt, solvate, or hydrate thereof, wherein R$^{12}$, R$^{13}$, and R$^{14}$ are each independently selected from hydrogen, halogen, alkyl, alkenyl, alkynyl, heterocyclyl, aryl, —OR$^A$, —OC(O)R$^A$, —SR$^A$, —N(R$^B$)$_2$, —N(R$^A$)C(O)R$^A$, —C(O)N(R$^B$)$_2$, —CN, —NO$_2$, —C(O)R$^A$, —C(O)OR$^A$, —S(O)R$^A$, —SO$_2$R$^A$, —SO$_2$N(R$^B$)$_2$, and —NHSO$_2$R$^B$; or R$^{12}$ and R$^{13}$ are taken together with their intervening atoms to form a carbocycle or heterocycle;

each R$^A$ is independently selected from hydrogen, alkyl, alkenyl, alkynyl, heterocyclyl, and aryl; and each R$^B$ is independently selected from hydrogen, alkyl, alkenyl, alkynyl, heterocyclyl, and aryl, or two R$^B$ taken together with the intervening nitrogen form a heterocycle.

In certain embodiments, for Formula (VI) or (VII), R$^1$, R$^2$, R$^3$, R$^5$, R$^{12}$, R$^{13}$, and R$^{14}$ are each independently selected from —H, —OH, —Cl, —Br, —F, C$_{1-6}$ alkyl, C$_{1-6}$ alkoxy, alkynyl, aryl, —NO$_2$, —N(R$^B$)$_2$, —C(O)CH$_3$, —CO$_2$H, —C(O)OR$^A$, —C(O)N(R$^B$)$_2$, —CN, heterocyclyl, —SO$_2$-alkyl, and —SO$_2$-aryl. In certain embodiments, R$^1$, R$^3$, R$^5$, R$^{12}$, R$^{13}$, and R$^{14}$ are each independently selected from —H, —OH, —Cl, —Br, —F, methyl, ethyl, methoxy, ethoxy, —C≡C-aryl, phenyl, naphthyl, —NO$_2$, —NH—C$_{1-6}$ alkyl, —C(O)CH$_3$, —CO$_2$H, —CO$_2$Et, —CONH-aryl, —CN, N-morpholinyl, —SO$_2$-alkyl, and —SO$_2$-aryl.

In certain embodiments, R$^1$, R$^3$, R$^5$, R$^{12}$, R$^{13}$, and R$^{14}$ are each independently selected from hydrogen, —CO$_2$H, —C(O)OR$^A$, —C(O)N(R$^B$)$_2$, —OH, —NO$_2$, —CN, halogen, alkyl, aryl and heterocyclyl. In certain embodiments, R$^{12}$ and R$^{13}$ are taken together with their intervening atoms to form an optionally substituted heterocycle. In certain embodiments, R$^{12}$ and R$^{13}$ are taken together with their intervening atoms to form a succinimidyl ring.

In certain embodiments, R$^{12}$ and R$^{13}$ are each —CO$_2$H. In certain embodiments, R$^{12}$, R$^{13}$ and R$^{14}$ are each —CO$_2$H. In certain embodiments, R$^3$, R$^{12}$, R$^{13}$ and R$^{14}$ are each —CO$_2$H. In certain embodiments, R$^1$, R$^{12}$ and R$^{13}$ are each —CO$_2$H. In certain embodiments, R$^1$, R$^{12}$, R$^{13}$ and R$^{14}$ are each —CO$_2$H. In certain embodiments, R$^{15}$ is hydrogen.

In certain embodiments, R$^{12}$ and R$^{13}$ are each —CO$_2$H, and R$^{15}$ is hydrogen. In certain embodiments, R$^{12}$, R$^{13}$ and R$^{14}$ are each —CO$_2$H, and R$^{15}$ is hydrogen. In certain embodiments, R$^3$, R$^{12}$, R$^{13}$ and R$^{14}$ are each —CO$_2$H, and R$^{15}$ is hydrogen. In certain embodiments, R$^1$, R$^{12}$ and R$^{13}$ are each —CO$_2$H, and R$^{15}$ is hydrogen. In certain embodiments, R$^1$, R$^{12}$, R$^{13}$ and R$^{14}$ are each —CO$_2$H, and R$^{15}$ is hydrogen.

In certain embodiments, a compound employed by the present invention is a compound of Formula (I-a), (II), (III), (IV), (V), (VI), or (VII), wherein R$^2$ is not —C(O)R$^A$.

In certain embodiments, a compound employed by the present invention is a compound of Formula (I-a), (II), (III), (IV), (V), (VI), or (VII), wherein R$^2$ is not —C(O)CH$_3$.

In certain embodiments, a compound employed by the present invention is a compound of Formula (I-a), (II), (III), (IV), (V), (VI), or (VII), wherein R$^3$ is not —NH-allyl.

In certain embodiments, a compound employed by the present invention is a compound of Formula (I-a), (II), (III), (IV), (V), (VI), or (VII), wherein R$^2$ is not —NHCH$_2$CH$_2$OH.

In certain embodiments, a compound employed by the present invention is a compound of Formula (I-a), (II), (III), (IV), (V), (VI), or (VII), wherein R$^1$ and R$^4$ are not —NO$_2$.

In certain embodiments, a compound employed by the present invention is a compound of Formula (I-a), (II), (III), (IV), (V), (VI), or (VII), wherein when n is 2, each R$^5$ is not simultaneously methyl.

In certain embodiments, a compound of the present invention is one of the following:

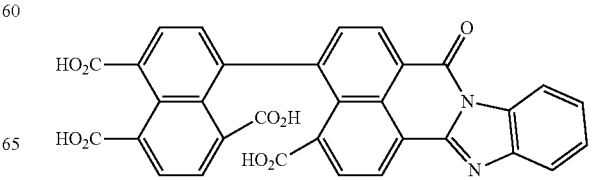

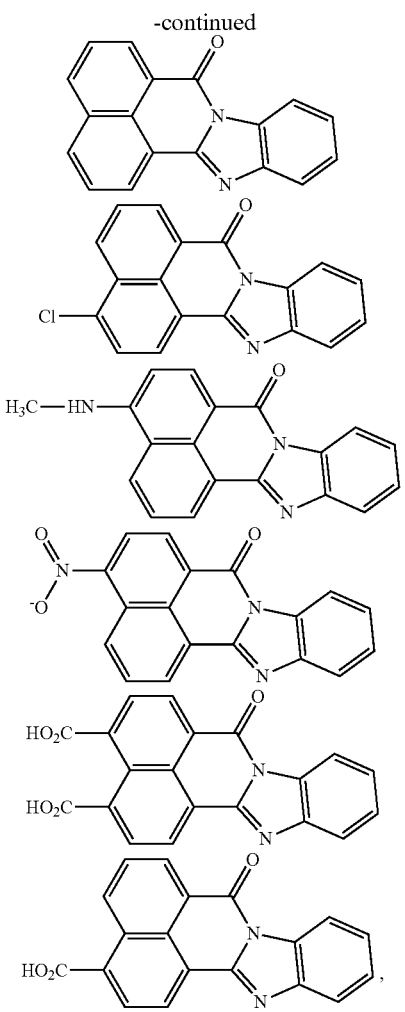

or a pharmaceutically acceptable salt, solvate, or hydrate thereof.

Pharmaceutical Compositions

Pharmaceutical compositions of the present invention and for use in accordance with the present invention may include a pharmaceutically acceptable excipient or carrier. As used herein, the term "pharmaceutically acceptable carrier" or "pharmaceutically acceptable excipient" means a non-toxic, inert solid, semi-solid or liquid filler, diluent, encapsulating material or formulation auxiliary of any type. *Remington's Pharmaceutical Sciences*, Sixteenth Edition, E. W. Martin (Mack Publishing Co., Easton, Pa., 1980) discloses various excipients used in formulating pharmaceutical compositions and known techniques for the preparation thereof. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and/or to animals, orally, rectally, parenterally, intracisternally, intravaginally, intranasally, intraperitoneally, topically (as by powders, creams, ointments, or drops), bucally, or as an oral or nasal spray.

Liquid dosage forms for oral administration include pharmaceutically acceptable emulsions, microemulsions, solutions, suspensions, syrups, and elixirs. In addition to the active ingredients (i.e., microparticles, nanoparticles, liposomes, micelles, polynucleotide/lipid complexes), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid dosage forms for oral administration include capsules, tablets, pills, powders, and granules. In such solid dosage forms, the particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols, and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Dosage forms for topical or transdermal administration of an inventive pharmaceutical composition include ointments, pastes, creams, lotions, gels, powders, solutions, sprays, inhalants, or patches. The particles are admixed under sterile conditions with a pharmaceutically acceptable carrier and any needed preservatives or buffers as may be required. Ophthalmic formulation, ear drops, and eye drops are also contemplated as being within the scope of this invention.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum coreum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Transdermal patches have the added advantage of providing controlled delivery of a compound to the body. Such dosage forms can be made by dissolving or dispensing the microparticles or nanoparticles in a proper medium. Absorption enhancers can also be used to increase the flux of the compound across the skin. The rate can be controlled by either providing a rate controlling membrane or by dispersing the particles in a polymer matrix or gel.

In certain embodiments, the compositions may be in the form of ointments, pastes, creams, lotions, gels, powders, solutions, sprays, inhalants. or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, poly-oxy-40-stearate. In certain embodiments, the active component is admixed under sterile conditions with a pharmaceutically acceptable excipient and any needed preservatives or buffers as may be required. Ophthalmic formulations, ear-drops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix (e.g., PLGA) or gel.

The ointments, pastes, creams, and gels may contain excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain excipients such as lactose, talc, silicic acid, aluminum hydroxide, calcium silicates, and polyamide powder, or mixtures of these substances. Sprays can additionally contain customary propellants such as chlorofluorohydrocarbons.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a provided compound may be administered concurrently with another agent effective against β-thalassemia or sickle cell disease), or they may achieve different effects (e.g., control of any adverse effects).

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a prodrug or other adduct or derivative of a compound of this invention which upon administration to a patient in need is capable of providing, directly or indirectly, a compound as otherwise described herein, or a metabolite or residue thereof.

Methods of Treatment

The present invention provides compounds that induce γ globin and can produce beneficial therapeutic effects. In certain embodiments, compounds and compositions described herein are used to treat hemoglobinopathies such as sickle cell anemia or β-thalassemia. In certain embodiments, a provided compound or composition is used to treat sickle cell anemia. In certain other embodiments, a provided compound or composition is used to treat β-thalassemia.

The inventive methods stimulate γ globin expression. In one aspect, the present invention provides methods comprising the compounds of the invention or compositions thereof for stimulating γ globin expression comprising: contacting a subject with a compound or a composition of the invention under conditions suitable to induce γ globin expression in the subject.

In certain embodiments, the present invention provides a method of inducing γ globin comprising: contacting a cell with an effective amount of a compound of formula (1-a), (II), (III), (IV), (V), (VI), or (VII). In certain embodiments, the present invention provides a method of inducing γ globin comprising: administering to a subject an effective amount of a compound of formula (I-a), (II), (III), (IV), (V), (VI), or (VII).

In certain embodiments, the present invention provides a method of treating β-thalassemia comprising: administering an effective amount of a provided compound or composition to a patient suffering from β-thalassemia.

In certain embodiments, the present invention provides a method of treating sickle cell anemia comprising: administering an effective amount of a provided compound or composition to a patient suffering from sickle cell anemia.

In certain embodiments, a provided compound or composition is administered orally. In certain embodiments, a provided compound or composition is administered parenterally. In certain embodiments, a provided compound or composition is administered in combination with an additional therapeutic agent.

The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex, and diet of the subject; the time of administration, mute of administration, and rate of excretion of the specific compound employed; the duration of the treatment; drugs used in combination or coincidental with the specific compound employed; and like factors well known in the medical arts (see, for example, Goodman and Gilman's *The Pharmacological Basis of Therapeutics*, Tenth Edition, A. Gilman, J. Hardman and L. Limbird, eds., McGraw-Bill Press, 155-173, 2001, which is incorporated herein by reference in its entirety).

Screening Methods

In one aspect, the present invention provides methods for identifying compounds that induce γ globin expression. In certain embodiments, the present invention provides a cell-based assay comprising incubating a test compound with an MEL cell containing human γ globin promoter linked to a first fluorescent reporter and human β globin promoter linked to a second fluorescent reporter, and determining fluorescence intensity compared to background signal. In certain embodiments, the dual fluorescence reporter plasmid is pmLAR-Gp-DsRed-Bp-d2EGFP. In certain embodiments, the present invention provides an MEL cell comprising MEL cell containing human γ globin promoter linked to a first fluorescent reporter and human β globin promoter linked to a second fluorescent reporter. In certain embodiments, the first fluorescent reporter is DsRed. In certain embodiments, the second fluorescent reporter is d2EGFP. In certain embodiments, the first fluorescent reporter is DsRed and the second fluorescent reporter is d2EGFP. In some embodiments, the fluorescence intensity measured in DsRed.

In certain embodiments, assays are provided to determine the ability of compounds to induce γ globin expression. In further embodiments, inventive compounds exhibit $EC_{50}$ values≤100 µM. In further embodiments, inventive compounds exhibit $EC_{50}$ values≤50 µM. In further embodiments, inventive compounds exhibit $EC_{50}$ values≤40 µM. In further embodiments, inventive compounds exhibit $EC_{50}$ values≤30 µM. In further embodiments, inventive compounds exhibit $EC_{50}$ values≤20 µM. In further embodiments, inventive compounds exhibit $EC_{50}$ values≤10 µM. In further embodiments, inventive compounds exhibit $EC_{50}$ values≤7.5 µM. In certain embodiments, inventive compounds exhibit $EC_{50}$ values≤5 µM. In further embodiments, inventive compounds exhibit $EC_{50}$ values≤2.5 µM. In certain embodiments, inventive compounds exhibit $EC_{50}$ values≤1 µM. In certain embodiments, inventive compounds exhibit $EC_{50}$ values≤0.75 µM. In certain embodiments, inventive compounds exhibit $EC_{50}$ values≤0.5 µM. In certain embodiments, inventive compounds exhibit $EC_{50}$ values≤0.25 µM. In certain embodiments, inventive compounds exhibit $EC_{50}$ values≤0.1 µM. In further embodiments, inventive compounds exhibit $EC_{50}$ values≤75 nM. In further embodiments, inventive compounds exhibit $EC_{50}$ values≤50 nM. In further embodiments, inventive compounds exhibit $EC_{50}$ values≤25 nM. In further embodiments, inventive compounds exhibit $EC_{50}$ values≤10 nM. In other embodiments, exemplary compounds exhibit $EC_{50}$ values≤5 nM. In other embodiments, exemplary compounds exhibit $EC_{50}$ values≤1 nM.

According to the present invention, compounds may be assayed in any of the available assays known in the art for identifying inducers of γ globin. For example, the assay may be in vivo or in vitro, or high- or low-throughput format.

These and other aspects of the present invention will be further appreciated upon consideration of the following Examples, which are intended to illustrate certain particular embodiments of the invention but are not intended to limit its scope, as defined by the claims.

EXAMPLES

We have established a dual fluorescence reporter assay system to screen for the potential HbF-inducing agents. Taking advantage of fluoresence signal detected by fluorometer, we could quickly survey these chemical compounds to determine which ones switch-on the fetal γ globin promoter. This dual fluoresence reporter system has led us to identify several heterocyclic compounds with common core structure (benzo [de]benzo[4,5]imidazo[2,1-a]isoquinolin-7-one) and with higher efficacies/specificities in the induction of the embryonic/fetal globin chains. These chemical compounds may be developed into a new generation of therapeutical drugs for the cure of hemoglobinopathies including sickle cell disease and β-thalassemia (e.g., β-thalassemia major).

Materials and Methods

Chemical Compounds.

All of the heterocyclic compounds screened including compound A (8-(3-Carboxy-7-oxo-7H-benzo[de]benzo[4,5] imidazo[2,1-a]isoquinolin-4-yl)-naphthalene-1,4,5-tricarboxylic acid, compound B (Benzo[de]benzo[4,5]imidazo[2, 1-a]isoquinolin-7-one), compound C (3-Chloro-benzo[de] benzo[4,5]imidazo[2,1-a]isoquinolin-7-one), compound D (4-Nitro-benzo[de]benzo[4,5]imidazo[2,1-a]isoquinolin-7-one), compound E (4-Methylamino-benzo[de]benzo[4,5] imidazo[2,1-a]isoquinolin-7-one), and compound F (7-Oxo-7H-benzo[de]benzo[4,5]imidazo[2,1-a]isoquinoline-3,4-dicarboxylic acid) were purchased from ChemDiv Co. The selective CaMKK inhibitor STO-609 (7-oxo-7H-benzimidazo[2,1-a]benz[de]isoquinoline-3-carboxylic acid acetate) was purchased from Sigma-Aldrich.

Reporter Constructs.

The reporter plasmid pmLAR-Gp-DsRed-Bp-d2EGFP was constructed by multiple steps of subcloning process. In brief, an 8,003 bp fragment of mini-LAR (mLAR; the minimal locus activating region which contains HS4-HS3-HS2-HS1 cis-acting elements for regulating human β-like globin genes expression) excised from pLAR-13 was inserted into the XhoI and EcoRI sites of pd2EGFP-1. Then a 1,622 bp β globin promoter (Bp) fragment was generated by PCR amplification and cloned into the AgeI site of pd2EGFP-1 to generate pmLAR-Bp-d2EGFP. A 1,377 bp γ globin promoter (Gp) fragment was also subcloned into the AgeI site of pDsRed-Monomer-C1 vector to generate pGp-DsRed-Cl. The Gp-DsRed fragment was then excised from the pGp-DsRed-C1 plasmid and re-inserted into the SalI site in between the mLAR and Bp-d2EGFP of pmLAR-Bp-d2EGFP. The resulting reporter pmLAR-Gp-DsRed-Bp-d2EGFP was then used for establishing stable cell lines by transfection into the MEL cells.

Cell Cultures and Stable Cell Line Establishment.

Mouse erythroleukemic (MEL) cells, an adult erythroid cell line (Friend, et al. (1971) *Proc Natl Acad Sci USA* 68:378-82), were maintained in DMEM medium (Gibco) supplemented with 10% FBS and 1% penicillin-streptomycin, in 37° C. chamber under a 5% $CO_2$ humidified atmosphere. For establishing stable cell lines, transfection of the reporter pmLAR-Gp-DsRed-Bp-d2EGFP into MEL cells was carried out using the Neon™ transfection system (Invitrogen). $2 \times 10^6$ MEL cells were transfected with 5 μg of the plasmid. Following microporation, the MEL cells were seeded in 10 ml antibiotics-free DMEM for 24 hrs and selected with 700 mg/ml of neomycin for one month. The primary human erythroid culture was initiated by maintaining the purified mononuclear cells in SFEM medium with 1× cc100 cytokine mix (StemSpan) for 7 days. The cells were then kept in the differentiation medium (SFEM with 20 ng/ml SCF, 1 U/ml EPO, 5 ng/ml IL-3, 2 micromolar dexamethasone) for another 7 days at a density of $0.1-1 \times 10^6$ cells/ml. The cells were treated with chemical compound at day 7 post-differentiation and then harvested for further analysis after 3 days of compound treatment.

Robotic Screening of Chemical Compounds.

$5 \times 10^4$ MEL cells carrying the dual fluorescence reporter were seeded on optical Packard 96-well view plates, treated with 10 mM of the individual compound for 3 days, and primary screened for their DsRed intensity with use of the Wallac Victor3 1420 multilabel counter (Ex: 550/9; Em: 620). The secondary screenings were performed using a digital image detector, Cellomics Arrayscan 3.0 system, which doubly confirmed the intracellular DsRed fluorescence induced by the compound treatment. The endogenous globin gene expression patterns in the positive MEL cells from the primary and secondary screens as well as in compound-treated primary human erythroid cultures were subsequently identified by real time RT-PCR analysis.

Real Time RT-PCR Analysis.

Total RNAs were isolated with use of the RNAspin Mini kit (GE Healthcare). cDNA synthesis was carried out using SuperScript II reverse transcriptase (Invitrogen). Quantitative RT-PCR was performed using the SYBR Green PCR Master Mix (Applied Biosystems) and ABI 7500 real-time System. All data were analyzed after normalization to the expression level of the mouse or human 13 actin gene.

Results

Establishment of a High-Throughput Screening System for Surveying the Embryonic/Fetal Globin Gene-Inducing Chemical Compounds.

Figures 1, 5A:
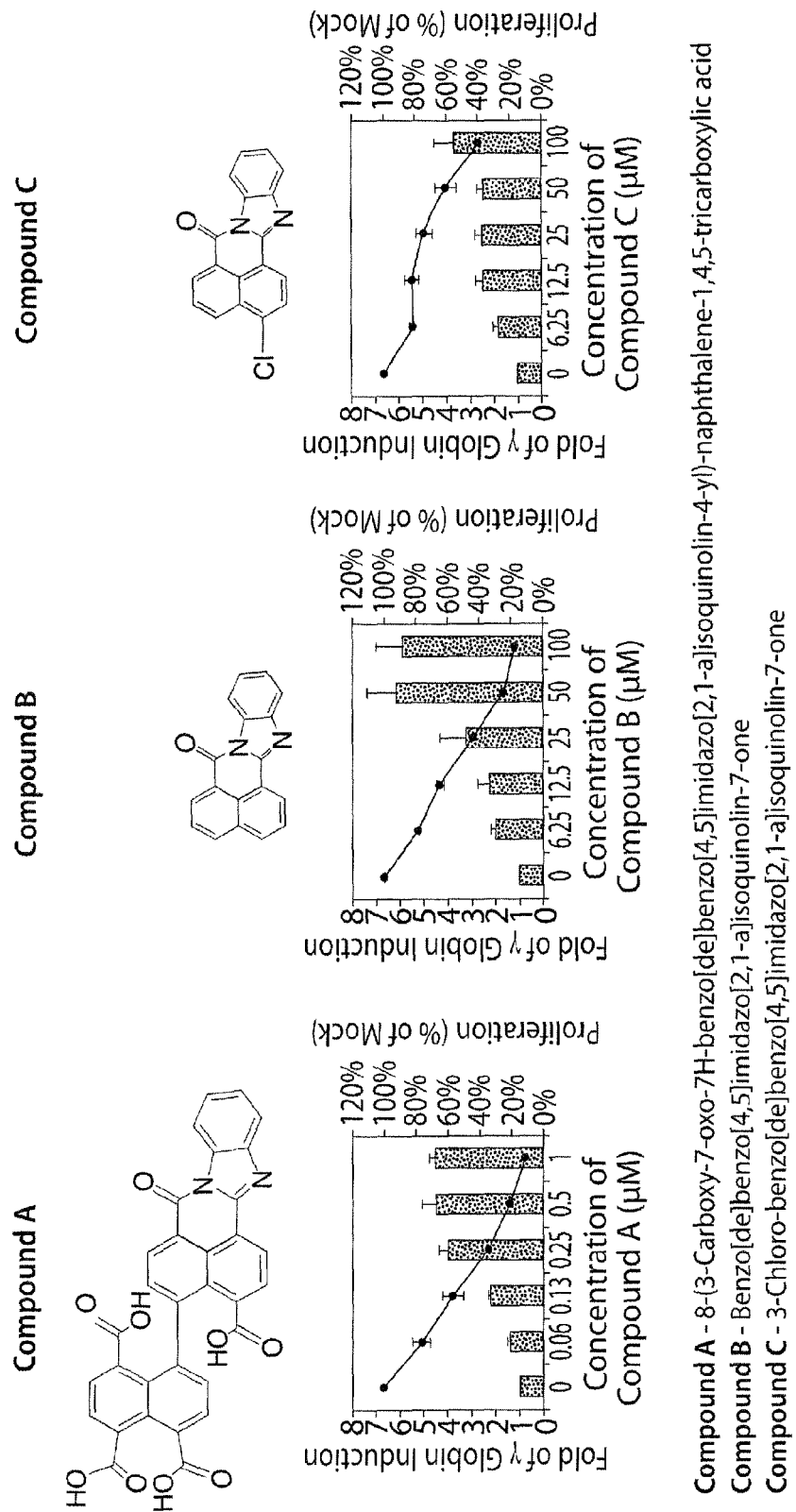
Figures 2, 5A:
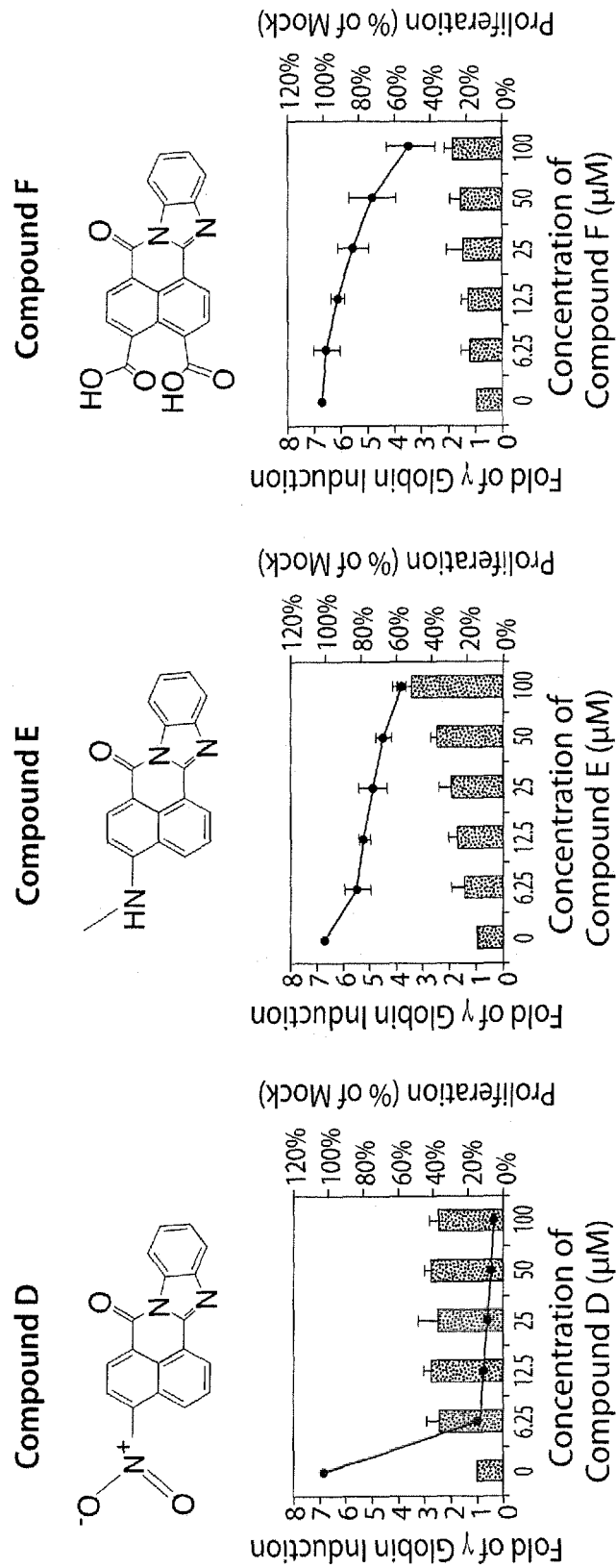
FIG. 2 shows results from high-throughput screening of compounds capable of inducing the embryonic/fetal globin genes. (A) Physical map of the dual fluorescence reporter plasmid. (B) Experimental procedures for the high-throughput screening. (Step 1) Ten thousand heterocyclic compounds were plated into 96-well culture plate and tested for their abilities to enhance embryonic/fetal globin promoters at a working concentration of 10 µM. (Step 2 & 3) The elevated expression of the DsRed fluorescence was detected by a fluoresence reader and further confirmed by a digital image detector. (Step 4) The activation of the endogenous embryonic/fetal globin genes as induced by the compound(s) was then verified by real-time RT-PCR analysis. (C) The screening data are shown in a dot-plot. Eight out of the 10,000 or so compounds were found to increase the DsRed fluorescence intensity by 1.5 fold or more. Real-time RT-PCR analysis showed that only one of the 8 compounds (compound A; arrowhead) induced the endogenous mouse embryonic εy globin mRNA expression level in MEL cells by more than 10-fold.

For the purpose of high-throughput screening of chemicals inducing the expression of embryonic/fetal globin genes, we have constructed a dual fluorescence reporter with both human γ globin promoter and β globin promoter built-in. Downstream the recombinant locus control region (mLAR), the order of γ globin promoter and β globin promoter were organized as their parental arrangements in the chromosomal β-like globin locus. The NCBI GenBank ID of the human β globin gene locus is NG_000007. The plasmid pmLAR-Gp-DsRed-Bp-d2EGFP carried the DsRed and d2EGFP fluorescence genes as their reporters for monitoring the expression of γ and β globin genes, respectively (FIG. 2A). We have compared the fluorescence signals from the reporters with the endogenous globin expression patterns in erythroid cells at different developmental stages. The expression of fluorescence signals indeed reflected the status of expression patterns of the corresponding endogenous globin genes in the MEL and K562 cells.

Subsequently, the dual fluorescence reporter plasmid was used for the high-throughput screening of chemical compounds (FIG. 2B). In brief, ten thousand chemical compounds were chosen for testing their abilities to enhance the embryonic/fetal globin promoters at a working concentration of 10 μM. The elevated expression of the fluorescence was detected by a fluorescence reader and digital image detector. The screening results are showed in the dot-plot in FIG. 2C. Eight of the 10,000 compounds showed at least 1.5-fold increase of the red fluorescence intensity when compared to the background signal. The activations of the endogenous embryonic/fetal globin chains as induced by these compounds were further verified by real-time RT-PCR analysis. The data showed that only one compound (compound A; arrowhead in FIG. 2C) induced more than 10-fold of the mouse embryonic (εγ) globin mRNA expression in MEL cells.

The sequences of mLAR, γ globin promoter, and β globin promoter are as follows:

mLAR (8003 bp, SEQ ID NO: 1):
tcgactctagaggatcaattcgagctcttggggaccccagtacacaagaggggacgcagggtatatgtagacatctcattcttttttcttag tgtgagaataagaatagccatgacctgagtttatagacaatgagccctttctctctcccactcagcagctatgagatggcttgccctgcct ctctactaggctgactcactccaaggcccagcaatgggcagggctctgtcagggctttgatagcactatctgcagagccagggccga gaaggggtggactccagagactctccctcccattcccgagcagggtttgcttatttatgcatttaaatgatatatttattttaaaagaaataa caggagactgcccagccctggctgtgacatggaaactatgtagaatattttgggttccattttttttccttctttcagttagaggaaagggg gctcactgcacatacactagacagaaagtcaggagctttgaatccaagcctgatcatttccatgtcatactgagaaagtccccacccttct ctgagcctcagtttctcttttataagtaggagtctggagtaaatgatttccaatggctctcatttcaatacaaaatttccgtttattaaatgcat gagcttctgttactccaagactgagaaggaaattgaacctgagactcattgactggcaagatgtccccagaggctctcattcagcaataa aattctcaccttcacccaggcccactgagtgtcagatttgcatgcactagttcacgtgtgtaaaaaggaggatgcttctttcctttgtattctc acatacctttaggaaagaacttagcacccttcccacacagccatcccaataactcatttcagtgactcaaccccttgactttataaaagtctt gggcagtatagagcagagattaagagtacagatgctggagccagaccacctgagtgattagtgactcagtttctcttagtaattgtatga ctcagtttcttcatctgtaaaatggagggttttttaattagtttgttttgagaaagggtctcactctgtcacccaaatgggagtgtagtggca aaatctcggctcactgcaacttgcacttcccaggctcaagcggtcctcccacctcaacatcctgagtagctggaaccacaggtacacac caccatacctcgctaattttttgtatttttggtagagatggggtttcacatgttacacaggatggtctcagactccggagctcagaagagtc aagcatttgcctaaggtcggacatgtcagaggcagtgccagacctatgtgagactctgcagctactgctcatgggccctgtgctgcact gatgaggaggatcagatggatggggcaatgaagcaaaggaatcattctgtggataaaggagacagccatgaagaagtctatgactgt aaatttgggagcaggagtctctaaggacttggatttcaaggaattttgactcagcaaacacaagaccctcacggtgactttgcgagctg gtgtgccagatgtgtctatcagaggttccagggagggtgggtgggtcagggctggccaccagctatcagggcccagatgggttat aggctggcaggctcagataggtggttaggtcaggttggtggtgctgggtggagtccatgactcccaggagccaggagagatagacc atgagtagagggcagacatgggaaggtgggggaggcacagcatagcagcattttttcattctactactacatgggactgctcccctat accccagctagggcaagtgccttgactcctatgttttcaggatcatcatctataaagtaagagtaataattgtgtctatctcatagggtta ttatgaggatcaaaggagatgcacactctctggaccagtggcctaacagttcaggacagagctatgggcttcctatgtatgggtcagtg gtctcaatgtagcaggcaagttccagaagatagcatcaaccactgttagagatatactgccagtctcagagcctgatgttaatttagcaat gggctgggaccctcctccagtagaaccttctaaccaggatccagtggggcctctaagactaagtcactctgtctcactgtgtcttagcca gttccttacagcttgccctgatgggagatagagaatgggtatcctccaacaaaaaaataaattttcatttctcaaggtccaacttatgttttct taatttttaaaaaaatcttgaccattctccactctctaaaataatccacagtgagagaaacattcttttcccccatcccataaatacctctatta aatatgaaaatctgggcatggtgtctcacacctgtaatcccagcactttgggaggctgaggtgggtggactgcttggagctcaggagt tcaagaccatcttggacaacatggtgataccctgcctctacaaaaagtacaaaaattagcctggcatggtggtgtgcacctgtaatccca gctattgggtggctgaggcaggagaattgcttgaacccgggaggcggaggttgcagtgagctgagatcgtgccactgcactccag cctggggacagagcacattataattaactgttatttttacttggactcttgtggggaataagatacatgttttattcttatttatgattcaagc actgaaaatagtgtttagcatccagcaggtgcttcaaaaccatttgctgaatgattactatacttttacaagctcagctccctctatcccttc cagcatcctcatctctgattaaataagcttcagttttccttagttcctgttacatttctgtgtgtctccattagtgacctcccatagtccaagca tgagcagttctggccaggcccctgtcggggtcagtgccccaccccgccttctggttctgtgtaaccttctaagcaaaccttctggctca agcacagcaatgctgagtcatgatgagtcatgctgaggcttagggtgtgtgcccagatgttctcagcctagagtgatgactcctatctgg gtccccagcaggatgcttacagggcagatggcaaaaaaaggagaagctgaccacctgactaaaactccacctcaaacggcatcat aaagaaaatggatgcctgagacagaatgtgacatattctagaatatatttttcctgaatatatatatatatatatacacatatacgtatata tatatatatatatatttgttgttatcaattgccatagaatgattagttattgtgaatcaaatatttatcttgcaggtggcctctatacctagaag cggcagaatcaggctttattaatacatgtgtatagattttaggatctatacacatgtattaatatgaaacaaggatatggaagaggaaggc atgaaaacaggaaaagaaaacaaaccttgtttgccatttaaggcacccctggacagctaggtggcaaaaggcctgtgctgttagagg -continued

```
acacatgctcacatacgggtcagatcaattctgtctgattgttctctgacttatctaccattttccctccttaaagaaactgtggaacttcctt cagctagaggggcctggctcagaagcctctggtcagcatccaagaaatacttgatgtcactttggctaaaggtatgatgtgtagacaag ctccagagatggtttctcatttccatatccacccacccagctttccaattttaaagccaattctgaggtagagactgtgatgaacaaacacc ttgacaaaattcaacccaaagactcactttgcctagcttcaaaatccttactctgacatatactcacagccagaaattagcatgcactaga gtgtgcatgagtgcaacacacacacaccaattccatattctctgtcagaaaatcctgttggttttttcgtgaaaggatgttttcagaggct gaccccttgccttcacctccaatgctaccactctggtctaagtcactgtcaccaccacctaaattatagctgttgactcataacaatcttcct gcttctaccactgccccactacaatttcttcccaatatactatccaaattagtcttttcaaaatgtaagtcatatatggtcacctctttgttcaaa gtcttctgatagtttcctatatcatttataataaaaccaaatccttacaattctctacaatagttgttcatgcatatattatgtttattacagatacg catatatatagctctcatataaataaatatatatatttatgtgtatgtgtgtagagtgttttttcttacaactctatgatgtaggtattattagtgtcc caaattttataatttaggacttctatgatctcatcttttattctcccccttcaccgaatctcatcctacattggccttattgatattccttgaaaattct aagcatcttacatctttagggtatttacatttgccattccctatgccctaaatatttaatcatagtttcatataaatgggttcctcatcatctatgg gtactctctcaggtgttaactttatagtgaggactttcctgccatactacttaaagtagcgatacccttcaccctgtcctaatcacactctgg ccttcatttcagttttttttttttctccatagcacctaatctcattggtatataacatgtttcatttgcttatttaatgtcaagctctttccactatcaag tccatgaaaacaggaactttattcctctattctgttttgtgctgtattcttagcaattttacaattttgaatgaaatgaatgagcagtcaaacac atatacaactataattaaaaggatgtatgctgacacatccactgctatgcacacaaagaaatcagtggagtagagctggaagcgcta agcctgcatagagctagttagccctccgcaggcagagccttgatgggattactgagttctagaattggactcatttgttttgtaggctgag atttgctcttgaaaacttgttctgaccaaaataaaaggctcaaaagatgaatatcgaaaccagggtgttttttacactggaatttataactag agcactcatgtttatgtaagcaattaattgtttcatcagtcaggtaaaagtaaagaaaaactgtgccaaggcaggtagcctaatgcaatat gccactaaagtaaacattattccataggtgtcagatatggcttattcatcatcttcatgggaaggatggccttggcctggacatcagtgtt atgtgaggttcaaaacacctctaggctataaggcaacagagctccttttttttttttctgtgctttcctggctgtccaaatctctaatgataagc atacttctattcaatgagaatattctgtaagattatagttaagaattgtgggagccattccgtctcttatagttaaatttgagcttcttttatgatc actgttttttaatatgctttaagttctggggtacatgtgccatggtggtttgctgcacccatcaacccgtcatctacattaggtatttctcctaa tgctatccttcccctagcccccacccccaacaggccccagtgtgtgatgttccctccctgtgtccatggatcactggttttttttttttttttt tttttttttttaaagtctcagttaaattttggaatgtaatttattttcctggtatcctaggacctgcaagttatctggtcactttagccctcacgtttt gatgataatcacatatttgtaaacacaacacacacacacacacacacatatatatataaaacatatatatacataaacacacata acatatttatcgggcatttctgagcaactaactcatgcaggactctcaaacactaacctatagccttttctatgtatctacttgtgtagaaacc aagcgtggggactgagaaggcaatagcaggagcattctgactctcactgcctttggctaggtccctccctcatcacagctcagcatagt ccgagctcttatctatatccacacacagtttctgacgctgcccagctatcaccatcccaagtctaaagaaaaaataatgggtttgcccat ctctgttgattagaaaacaaaacaaataaaataagcccctaagctcccagaaaacatgactaaaccagcaagaagaagaaaatacaa taggtatatgaggagactggtgacactagtgtctgaatgaggcttgagtacagaaagaggctctagcagcatagtggtttagaggag atgtttctttccttcacagatgccttagcctcaataagcttgcggttgtggaagtttactttcagaacaaactcctgtggggctagaattattg atggctaaaagaagcccgggggagggaaaaatcattcagcatcctcacccttagtgacacaaaacagagggggcctggttttccatat ttcctcatgatggatgatctcgttaatgaaggtggtctgacgagatcattgcttcttccatttaagccttgctcacttgccaatcctcagtttta accttctccagagaaatacacatttttattcaggaaacatactatgttatagtttcaatactaaataatcaaagtactgaagatagcatgcat aggcaagaaaaagtccttagctttatgttgctgttgtttcagaatttaaaaaagatcaccaagtcaaggacttctcagttctagcactagag gtggaatcttagcatataatcagaggttttcaaaatttctagacatgagattcaaagccctgcacttaaaatagtctcatttgaattaactctt tatataaattgaaagcacattctgaactacttcagagtattgttttatttctatgttcttagttcataaatacattaggcaatgcaatttaattaaa aaaacccaagaatttcttagaattttaatcatgaaaataaatgaaggcatctttacttactcaaggtcccaaaaggtcaaagaaaccagga aagtaaagctatatttcagcggaaaatgggatatttatgagttttctaagttgacagactcaagttttaaccttcagtgcccatgatgtagga aagtgtggcataactggctgattctggctttctactcctttttcccattaaagatccctcctgcttaattaacattcacaagtaactctggttgt
```

-continued
```
actttaggcacagtggctcccgaggtcagtcacacaataggatgtctgtgctccaagttgccagagagagagattactcttgagaatga gcctcagccctggctcaaactcacctgcaaacttcgtgagagatgaggcagaggtacactacgaaagcaacagttagaagctaaatg atgagaacacatggactcatagagggaaacaacgcatactggggcctatcagagggtggagggtgagagaaggagaggatcagg aaaaatcactaatggatgctaagcgtaatacctgagtgatgagatcatctatacaacaaaccccttgacattcatttatctatgtaacaaa cctgcacatcctgtacacgtacccctgaacttaaaataaaagttgaaaacaagaaagcaacagtttgaacacttgttatggtctattctctc attctttacaattacactagaaaatagccacaggctcctgcaaggcagccacagaatttatgacttgtgatgatctaatgctttcataaaga agcaaatataataaatactataccacaaatgtaatgtttgatgtctgataatgatatttcagtgtaattaaacttagcactcctatgtatattattt gatgcaataaaaacatattttttttagcacttacagtctgccaaactggcctgtgacacaaaaaaagtttag
```
γ globin promoter (1377 bp, SEQ ID NO: 2):
```
tacacaggatcatgaaggatgaaagaacttcaccaatattataataatttcaatcaacctgatagcttaggggataaactaatttgaagata cagcttgcctccgataagccagaattccagagcttctggcattataatctagcaaggttagagatcatggatcactttcagagaaaaaca aaaacaaactaaccaaaagcaaaacagaaccaaaaaaccaccataaatacttcctaccctgttaatggtccaatatgtcagaacagc gctgtgttagaaataaagctgtctaaagtacactaatattcgagttataatagtgtgtggactattagtcaataaaaacaacccttgcctcttt agagttgttttccatgtacacgcacatcttatgtcttagagtaagattccctgagaagtgaacctagcatttatacaagataattaattctaat ccacagtacctgccaaagaacattctaccatcatctttactgagcatagaaggctacgccaaaaccctgggtcatcagccagcacaca cacttatccagtggtaaatacacatcatctggtgtatacatacatacctgaatatggaatcaaatattttttctaagatgaaacagtcatgattt atttcaaataggtacggataagtagatattgaggtaagcattaggtcttatattatgtaacactaatctattactgcgctgaaactgtggcttt atagaaattgttttcactgcactattgagaaattaagagataatggcaaaagtcacaaagagtatattcaaaagaagtatagcacttttttc cttagaaaccactgctaactgaaagagactaagatttgtcccgtcaaaaatcctggacctatgcctaaaacacatttcacaatccctgaac ttttcaaaaattggtacatgctttagctttaaactacaggcctcactggagctagagacaagaaggtaaaaaacggctgacaaagaagt cctggtatcctctatgatgggagaaggaaactagctaaagggaagaataaattagagaaaaactggaatgactgaatcggaacaagg caaaggctataaaaaaattaagcagcagtatcctcttgggggccccttccccacactatctcaatgcaaatatctgtctgaaacggtcc ctggctaaactccacccatgggttggccagccttgccttgaccaatagccttgacaaggcaaacttgaccaatagtcttagagtatccag tgaggccaggggccggcggctggctagggatgaagaataaaaggaagcacccttcagcagttccacacactcgcttctggaacgtc tgaggttatcaataagc
```
β globin promoter (1622 bp, SEQ ID NO: 3):
```
gtcgactctagaggatctctatttatttagcaataatagagaaagcatttaagagaataaagcaatggaaataagaaatttgtaaatttcctt ctgataactagaaatagaggatccagtttcttttggttaacctaaattttatttcattttattgttttattttattttattttattttgtgtaat cgtagtttcagagtgttagagctgaaaggaagaagtaggagaaacatgcaaagtaaaagtataacactttccttactaaaccgactgggtttcc aggtagggcaggattcaggatgactgacagggcccttagggaacactgagaccctacgctgacctcataaatgcttgctacctttgct gttttaattacatcttttaatagcaggaagcagaactctgcacttcaaaagttttttcctcacctgaggagttaatttagtacaagggaaaaa gtacaggggatgggagaaaggcgatcacgttgggaagctatagagaaagaagagtaaatttttagtaaaggaggtttaaacaaacaa aatataaagagaaataggaacttgaatcaaggaaatgattttaaaacgcagtattcttagtggactagaggaaaaaaataatctgagcca agtagaagaccttttcccctcctaccccactttctaagtcacagaggcttttgttccccagacactcttgcagattagtccaggcagaa acagttagatgtccccagttaacctcctatttgacaccactgattacccccattgatagtcacactttgggttgtaagtgacttttatttatttgt atttttgactgcattaagaggtctctagttttttatctcttgtttcccaaaacctaataagtaactaatgcacagagcacattgatttgtatttattc tattttagacataatttattagcatgcatgagcaaattaagaaaaacaacaacaaatgaatgcatatatatgtatatgtatgtgtgtatatata cacatatatatatatttttttcttttcttaccagaaggttttaatccaaataaggagaagatatgcttagaactgaggtagagtttcatccat tctgtcctgtaagtattttgcatattctggagacgcaggaagagatccatctacatatcccaaagctgaattatggtagacaaagctcttcc
```

-continued

```
acttttagtgcatcaatttcttatttgtgtaataagaaaatttgggaaaacgatcttcaatatgcttaccaagctgtgattccaaatattacgtaa atacacttgcaaaggaggatgtttttagtagcaatttgtactgatggtatggggccaagagatatatcttagagggagggctgagggtttg aagtccaactcctaagccagtgccagaagagccaaggacaggtacggctgtcatcacttagacctcaccctgtggagccacaccta gggttggccaatctactcccaggagcagggagggcaggagccagggctgggcataaaagtcagggcagagccatctattgcttaca tttgcttctgacacaactgtgttcactagcaacctcaaacagacacc
```

Identification of Compound a Increasing the Expression of Human Embryonic/Fetal Globin Genes with Higher Efficacy and Specificity.

Figure 3A:
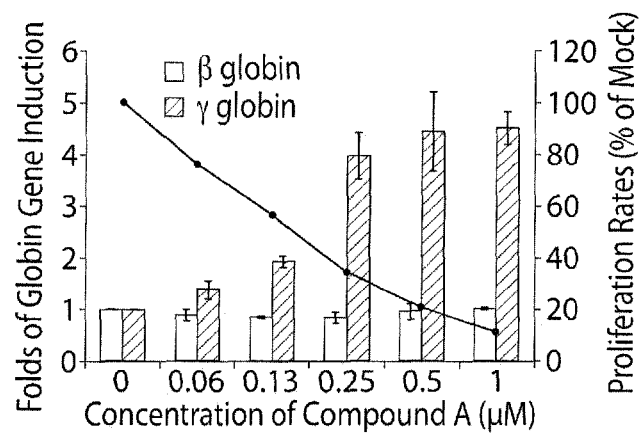
FIG. 3 illustrates induction of the endogenous globin genes in the primary culture of human erythroid progenitor cells by compound A. (A) Dosage effect of compound A in the differentiated human erythroid progenitor cells. The differentiated primary cultured cells were treated with different concentrations of compound A for 3 days. Total mRNA was extracted, and relative induction of the β and γ globin mRNAs was determined by real time RT-PCR analysis. The cell proliferation abilities were determined with use of alamar Blue reagent (mock control as 100%). The white bars indicated the relative expression levels of β-globin. The gray bars represent the relative levels of γ-globin mRNA. (B) Comparison of γ and β globin gene expression patterns in primary erythroid cultured cells treated with different fetal globin inducing agents. The cells were treated with compound A (0.25 µM), TSA (0.33 µM), hydroxyurea (HU; 100 µM), and sodium butyrate (NaB; 0.5 mM), respectively, for three days. The total RNAs were then isolated for real time RT-PCR analysis. Relative induction of the β globin gene (white bars) and the γ globin gene (grey bars) was then determined.

Next, we examined the endogenous globin gene induction by compound A in human erythroid progenitor cultures. The primary cultured cells were isolated from the peripheral blood of donors, expanded and differentiated for a total of 14 days in the culture medium, and treated with different concentrations of compound A for another 3 days. While the proliferation rates of the cells were in reverse relationship with the concentration of compound A, the relative expression level of the γ, but not β, globin gene was significantly increased as a function of increased concentrations of compound A (FIG. 3A).

Figure 3B:
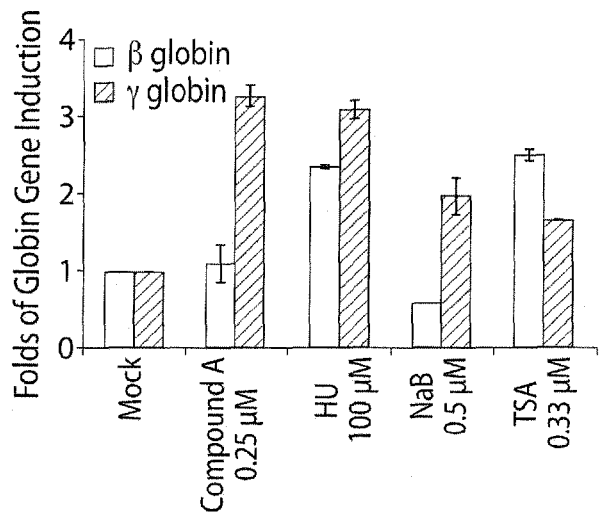

To further explore the unique features of compound A allowing it to induce the human embryonic/fetal globin genes in primary erythroid culture, we first compared the α-like globin expression patterns upon treatment with different fetal globin inducing agents in primary erythroid cultured cells. Interestingly, cells treated with compound A showed the highest γ-globin induction fold as compared to that of TSA, hydroxyurea (HU), and sodium butyrate (NaB), whereas only modest induction of the adult β globin gene expression by compound A was observed in comparison to HU and TSA (FIG. 3B).

The Identification of Transcription Regulators Involved in the Fetal Globin Gene Induction by Compound a Treatment.

Figure 4:
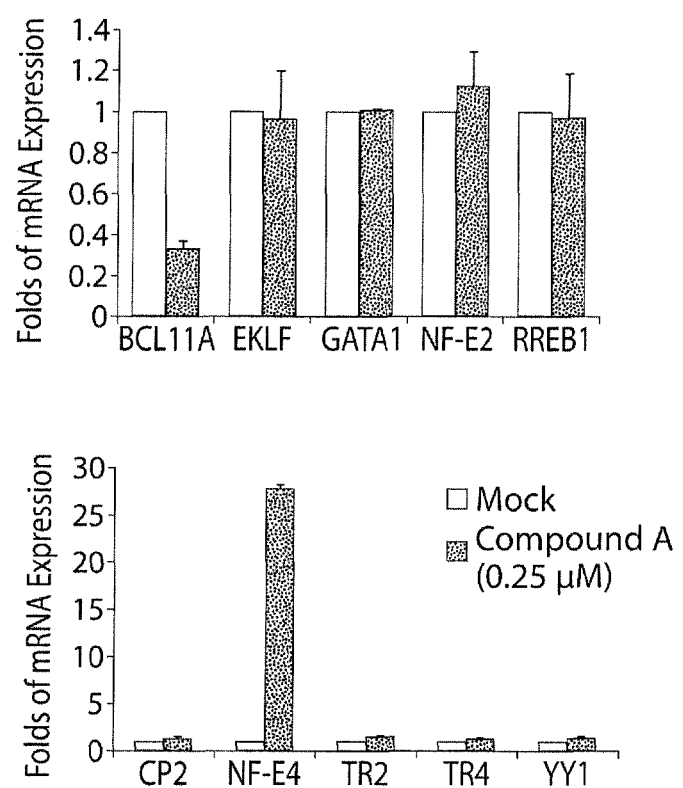
FIG. 4 shows relative expression levels of transcription factors associated with globin gene regulation. Primary human erythroid cultures were treated with 0.25 µM of compound A, and the relative expression levels of different transcription factors were then determined by real-time RT-PCR analysis. The white bars indicate the expression levels of mock control set as 1. The black bars are the relative expression levels in compound A-treated cells.

Several transcription factors, which include GATA1 (18), NF-E2 (3), EKLF (2), YY1 (22), TR2/TR4 (29), NF-E4 (7), RREB1 (4), and BCL11A (23), have been identified to serve as either activators or repressors for the globin gene expression. To uncover the molecular mechanisms how compound A might utilize to induce specifically the fetal γ globin gene expression, the relative expression levels of several transcription factors known to affect globin gene transcription were analyzed (FIG. 4). As seen, the level of the γ globin gene activator NF-E4 (7) was up-regulated in the primary human erythroid cultures treated with compound A. Meanwhile, the level of the γ globin gene repressor Bcl11a (23) was reduced. The expression levels of other globin gene regulators, such as EKLF, GATA1, NF-E2, RREB1, CP2, TR2/TR4, YY1, were not profoundly changed by compound A treatment. The elevation of NF-E4 and reduction of Bcl11a might both contribute to the activation of the γ globin gene expression in these compound A-treated erythroid cells.

Elevation of the Fetal γ Globin Expression by Chemical Compounds with Identical Heterocyclic Core Structure as Compound A Subsequently, we have surveyed 18 chemical compounds with similar heterocyclic structures to compound A. Five of these 18 heterocyclic compounds were identified to have the ability to induce fetal γ globin expression (FIG. 5, compound B—F). Interestingly, all six compounds (including compound A) share the identical core structure (benzo[de]benzo[4,5]imidazo[2,1-a]isoquinolin-7-one) and exerted comparable abilities of γ globin induction. The dosage effects of these heterocyclic compounds in the activation of γ globin gene expression and inhibition of cell proliferation are showed in FIG. 5.

Figure 6:
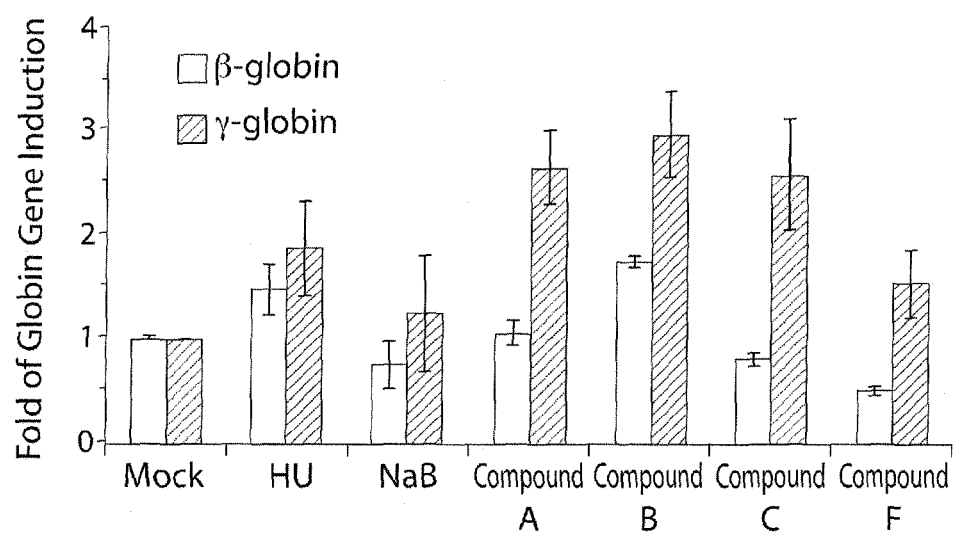
FIG. 6 illustrates induction of endogenous globin genes in primary erythroid cultures treated with different fetal γ globin-inducing agents (hydroxyurea (HU), sodium butyrate (NaB), and provided naphthoylenebenzimidazole compounds) at $IC_{50}$ for 3 days. The total mRNA was extracted, and relative induction of the β and γ globin mRNAs was determined by real time RT-PCR analysis. The white bars indicated the relative expression levels of β-globin. The gray bars represent the relative levels of γ-globin mRNA.
Figure 7A:
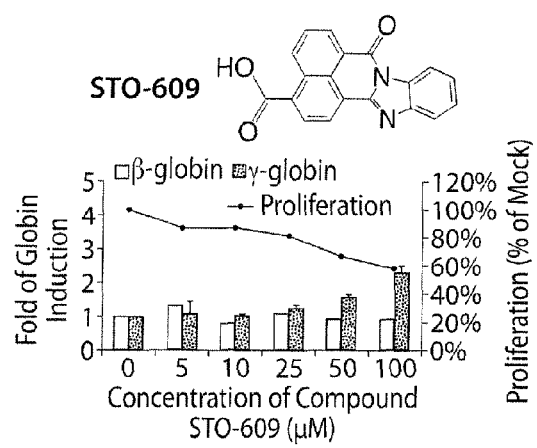
FIG. 7 shows induction of fetal γ globin gene expression in primary culture of human erythroid cells by the specific CaMKK inhibitor STO-609. Dosage effects of STO-609 on the proliferation and γ/β globin gene expression of differentiated human erythroid progenitor cells were analyzed as described for compounds A-F. The differentiated primary cultured erythroid cells were treated with different concentrations of STO-609 for 3 days. (A) Relative induction of β (white bars) and γ globin mRNAs (black bars) was determined by real time RT-PCR analysis. The proliferation curve of the cells is shown with the mock control being 100%. (B) Relative expression levels of NF-E4 were determined by real time RT-PCR analysis and shown by the grey bars. (C) Relative expression levels of Bcl11a in response to treatments with different concentrations of STO-609 are shown (white bars). (D) Relative expression levels of c-Myb in cells treated with different concentrations of STO-609 are shown (black bars). The mock control is set as 1.
Figure 7B:
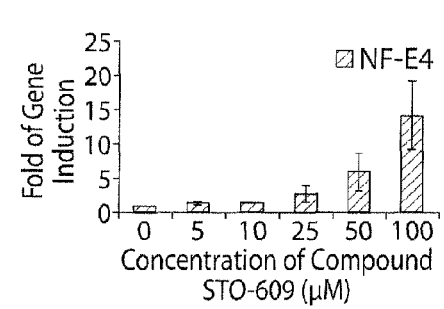
Figure 7C:
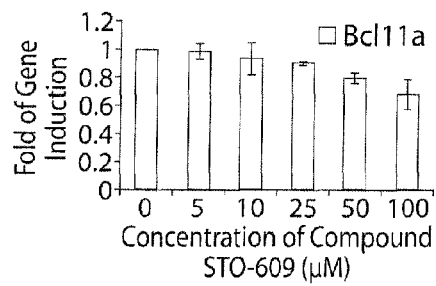
Figure 7D:
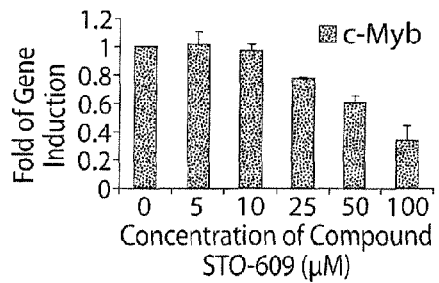

The relative induction folds of the endogenous β and γ globin genes by compounds B, C, and F at their $IC_{50}$ concentrations have been estimated by quantitative RT-PCR analysis and compared to those of compound A, HU, and NaB (FIG. 6). To obtain the whole picture of these heterocyclic compounds with respect to their induction capabilities of the individual globin chains, the absolute amount of the mRNA encoding each of the globins in human erythroid cells treated with HU, NaB, or compound A/B/C/F at $IC_{50}$ have also been estimated by absolute quantitative RT-PCR analysis. As seen in FIG. 9, the proportion of the γ globin mRNA was significantly increased from 8% to 10.7-19.6% after the heterocyclic compound treatment. Meanwhile, the proportion of the β globin mRNA was reduced from 87.2% to 73.8-81.4% after the heterocyclic compound treatment. Taken together, these heterocyclic compounds that we have identified preferentially induce the embryonic δ and fetal γ globin gene expression, but not the adult β globin (FIGS. 6 and 9).

The Comparison of the Fetal γ Globin Induction Abilities Between the Heterocyclic Compounds and Butyric Acid or Hydroxyurea To evaluate the fetal globin gene induction abilities of these heterocyclic compounds in comparison to NaB and HU, we have calculated the value of $IC_{50}$ (the half maximal inhibitory concentration) and EC (effective concentration) of these γ globin-inducing agents (FIG. 10). Of the two, $IC_{50}$ is the concentration of a compound that reduces the cell proliferation by 50%. EC is defined as the concentration of a compound that induces the γ globin mRNA level by 1.88 fold, the average fold of γ globin gene induction by HU at $IC_{50}$ in three sets of experiments. With different branched chains, these heterocyclic compounds showed quite different cytotoxicities ($IC_{50}$) as well as their effective dosages (EC). The therapeutic windows were then calculated as the ratios of the respective $IC_{50}$ and EC ($IC_{50}$/EC), which can be used to evaluate the benefits of these heterocyclic compounds among themselves and to HU and NaB ($4^{th}$ column from left, FIG. 10). Considering the therapeutic advantage (therapeutic windows), at least three of the compounds identified by us (compound B, C, and E) showed better therapeutical potential than that of HU or NaB. Furthermore, as seen in the most right column of the table in FIG. 10, all six compounds show similar or better capabilities to induce γ globin gene expression when compared to those of HU and NaB at $IC_{50}$. In certain embodiments, a composition according the present invention exhibits a larger therapeutic window than hydroxyurea. In certain embodiments, a composition according the present invention exhibits a larger therapeutic window than sodium butyrate.

Elevation of the Fetal γ Globin Expression by a CaMKK Inhibitor STO-609

Since the selective inhibitor for the Ca(2+)/calmodulin-dependent protein kinase kinase (CaMKK), STO-609 (30), contained the identical heterocyclic core structure (benzo[de]

benzo[4,5]imidazo[2,1-a]isoquinolin-7-one) as these fetal γ globin-inducing compounds described above, we next examined its potential to induce the fetal γ globin expression in human primary erythroid cells (FIG. 7). As anticipated, the expression level of the fetal γ globin gene, but not the adult β globin, was elevated upon treatment with STO-609 with a concentration of 50 mM or higher (FIG. 7A). As in the cases of the γ globin-inducing heterocyclic compounds A-F, the treatment with STO-609 also resulted in the transcriptional up-regulation of the γ globin gene activator NF-E4 (FIG. 7B). Concurrently, the expression level of the γ globin gene repressor Bcl11a was down-regulated by STO-609 (FIG. 7C). Moreover, we found that the transcript of c-Myb, another γ globin gene repressor (10), was also significantly reduced by the treatment of STO-609 (FIG. 7D). In conclusion, our data showed that these heterocyclic compounds including the specific CaMKK inhibitor STO-609, which possessed the same core structure (benzo[de]benzo[4,5]imidazo-[2,1-a]isoquinolin-7-one), all could function as efficient γ globin inducers. The activation of γ globin gene by these compounds seems to be triggered in part by modulating the expression levels of certain γ globin gene regulators, such as NF-E4, Bcl11a, and/or cMyb. The possible roles of these heterocyclic compounds including A-F and STO609, and their crosstalk with the program of fetal γ globin gene induction are discussed below.

Discussion

We have described above a high throughput screening system using a dual fluorescence reporter plasmid as the indicator for monitoring the endogenous globin genes expression. A similar approach has been reported and its use for assessment of the expression of the endogenous globin genes was well characterized (27). The specificity of such assay has been demonstrated in the screening of the HbF inducers. Taking advantage of this dual fluorescence assay system, we have been able to screen for chemical compounds that could induce the expression of the γ globin gene in adult erythroid cells. After surveying 10,018 compounds, we have identified six heterocyclic compounds, all of which include the same core structure (benzo[de]benzo[4,5]imidazo[2,1-a]isoquinolin-7-one), that display similar or better γ globin-inducing efficacies than that of HU or NaB at the concentrations of $IC_{50}$. Although these compounds exhibit diverse extents of cytotoxicities, all six heterocyclic compounds including compound A are able to induce the activation of the γ globin gene by 1.9 to 3.4 fold at $IC_{50}$ (FIG. 10). Furthermore, these heterocyclic compounds all exhibit high therapeutic windows ($IC_{50}$/EC), e.g., up to 10-fold by compound B, than hydroxyurea.

The fetal γ globin chain is able to functionally substitute for the defective 0 globin chain and helps to prevent the formation of HbS in sickle cell disease. The existence of fetal γ globin chain also balances the overloaded a globin chain and prevents its precipitation in the β-thalassemia patients. Thus, elevation of the γ globin amount would reduce the hemolysis in hemoglobinopathies patients and efficiently moderate the severity of anemia. A threshold of 10%-20% HbF expression is considered to be effective in modulating the clinical severity of hemoglobinopathies (21). As demonstrated in FIG. 9, compound A, B, C, and F induce the γ globin expression range up to 10.7-19.6% in primary erythroid cell culture, indicating that its HbF-inducing efficacy is comparable to that of other well-known fetal globin inducers, such as HU and NaB.

Figure 5B:
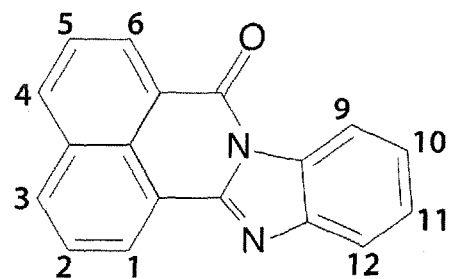
FIG. 5 illustrates induction of the fetal γ globin gene expression by six heterocyclic compounds with common core structure. (A) Several heterocyclic compounds with common napthoylenebenzimidazole core structure were selected to examine their abilities to induce γ globin gene expression in human primary cultured erythroid cells. Relative induction of the γ globin genes (black bars) by these compounds was then analyzed by real time RT-PCR. Cell proliferation abilities (the curves) were determined with use of alarmar Blue reagent (mock control as 100%). (B) Illustration of the common core structure (benzo[de]-benzo[4,5]imidazo[2,1-a]isoquinolin-7-one) and the numberings of its positions for possible modifications with branched side chains.

Since the six heterocyclic compounds we have identified as well as the specific CaMKK inhibitor STO-609 all share a common core structure, i.e. the structure of compound B (benzo[de]benzo[4,5]imidazo[2,1-a]isoquinolin-7-one), we anticipate that the naphthoylenebenzimidazole scaffold is very likely critical for up-regulating/inducing the γ globin gene expression. Furthermore, we have observed that the branched side chains of these compounds are located at either position 3 or position 4 of the heterocyclic structure (as shown in FIG. 5B) and that variations exist in both the efficacies and cytotoxicities among these compounds. Several compounds containing the same core structure (benzo[de]benzo-[4,5] imidazo[2,1-a]isoquinolin-7-one) with branched modifications at other positions display no detectable γ globin gene-induction ability (Table 1). These data suggest that modifications at certain positions, e.g. positions 3 and 4 of compound B, may lead to even better pharmaceutical development of compounds for therapies of sickle cell disease and severe β-thalassemia major.

TABLE 1

Screened compounds that displayed no detectable γ globin induction

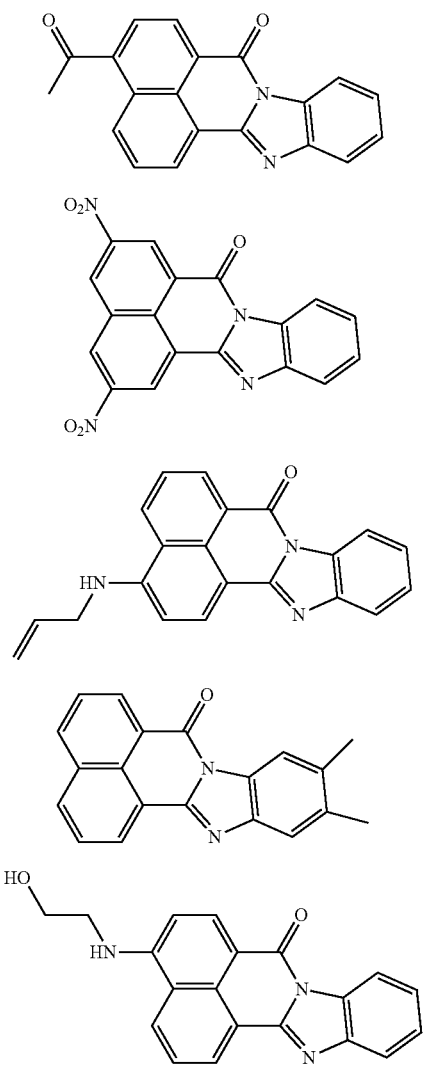

Interestingly, STO-609, the specific CaMKK inhibitor with the core structure as the heterocyclic compounds A-F, also displays the fetal γ globin-inducting capability. The inhibition of the cellular MEK/Erk pathway has been shown to stimulate the γ globin expression in human primary erythroid cells (14). Interestingly, the CaMKK signaling is linked to the MEK/Erk pathway through the downstream target of CaMKK, CaMKI (25). Thus, we believe that the repression of CaMKK activation by STO-609 likely triggers the inhibition of MEK/Erk signaling, thus resulting in the elevation of fetal γ globin gene expression. With identical core structure (Benzo[de]benzo[4,5]imidazo[2,1-a]isoquinolin-7-one), the heterocyclic compounds A-F that we have identified displayed similar capabilities with STO-609, such as fetal γ globin induction, NF-E4 mRNA up-regulation, and Bcl11a transcript (as well as cMyb mRNA) down-regulation. It is likely that the induction of fetal γ globin expression by these heterocyclic compounds is in part coupled to the inhibition of MEK/Erk signaling, as how the CAMKK inhibitor does.

Figure 8:
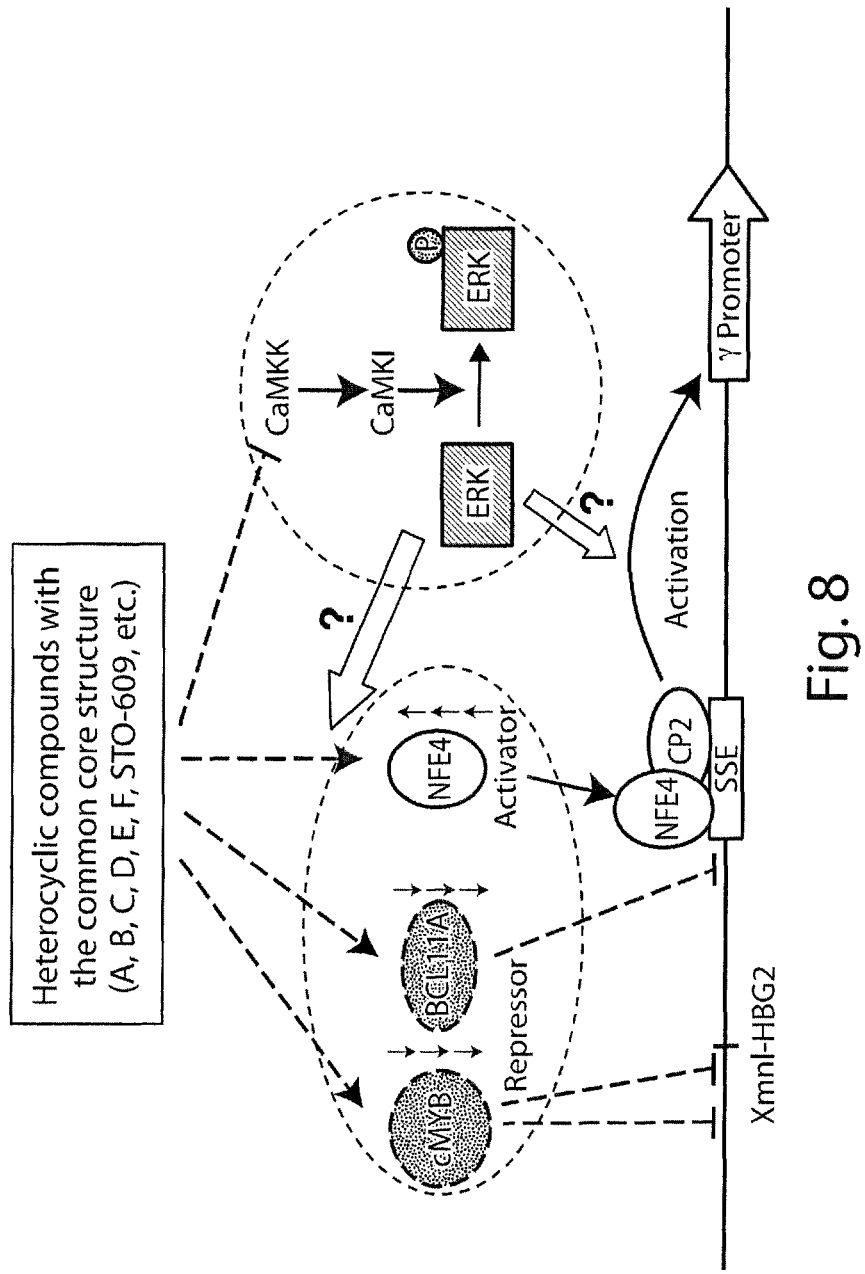
FIG. 8 shows a cartoon model illustrating the possible mechanisms of how the heterocyclic compounds with the same core structure activate the fetal γ globin gene expression. Our studies have shown that the fetal γ globin gene induction by these heterocyclic compounds is mediated at least in part by modulating the expression levels of several transcription factors, including up-regulation of the expression of NF-E4 and down-regulation of the Bcl11a as well as c-Myb. These heterocyclic compounds, as exemplified by STO-609, could also interfere with the activation of MEK/Erk signaling through CaMKK/CaMK1 pathway. It is likely that the CaMKK-inhibiting characteristics of the heterocyclic compounds with the core structure (benzo[de]benzo[4,5]imidazo[2,1-a]isoquinolin-7-one) contributes to the induction of the γ globin gene transcription.

In summary, our studies have revealed that a series of heterocyclic compounds with a common core structure (benzo[de]benzo[4,5]imidazo[2,1-a]isoquinolin-7-one) all could specifically induce the fetal γ globin expression in adult human erythroid cells. Moreover, we clarified the expression pattern of several γ globin regulators and presented here an illustration describing the mechanism how these heterocyclic compounds, including the specific CaMKK inhibitor STO-609, activate fetal γ globin expression (FIG. 8). We propose a model in which these heterocyclic compounds stimulate the expression of fetal γ globin chain by regulating the expression levels of NF-E4, Bcl11a, c-Myb, and/or interfering with the MEK/Erk signaling. The over-expression of NF-E4 (32), the down-regulation of Bcl11a (23), and the inhibition of MEK/Erk signaling pathway (14) all have been well demonstrated to induce the endogenous fetal γ globin expression. On the other hand, the over-expression of ectopic c-Myb was suggested to inhibit fetal γ globin gene expression (10). Thus, we believe that these compounds and their derivatives with appropriate modifications are invaluable for the development of a new generation of medicine for the cure of hemoglobinopathies, in particular sickle cell disease and severe β-thalassemia.

REFERENCES

1. Aljurf, M., L. Ma, E. Angelucci, G. Lucarelli, L. M. Snyder, C. R. Kiefer, J. Yuan, and S. L. Schrier. 1996. Abnormal assembly of membrane proteins in erythroid progenitors of patients with beta-thalassemia major. Blood 87:2049-56.
2. Bieker, J. J. 2005. Probing the onset and regulation of erythroid cell-specific gene expression. Mt Sinai J Med 72:333-8.
3. Bulger, M., T. Sawado, D. Schubeler, and M. Groudine. 2002. ChIPs of the beta-globin locus: unraveling gene regulation within an active domain. Curr Opin Genet Dev 12:170-7.
4. Chen, R. L., Y. C. Chou, Y. J. Lan, T. S. Huang, and C. K. Shen. Developmental silencing of human zeta-globin gene expression is mediated by the transcriptional repressor RREB1. J Biol Chem 285:10189-97.
5. Constantoulakis, P., G. Knitter, and G. Stamatoyannopoulos. 1989. On the induction of fetal hemoglobin by butyrates: in vivo and in vitro studies with sodium butyrate and comparison of combination treatments with 5-AzaC and AraC. Blood 74:1963-71.
6. Friend, C., W. Scher, J. G. Holland, and T. Sato. 1971. Hemoglobin synthesis in murine virus-induced leukemic cells in vitro: stimulation of erythroid differentiation by dimethyl sulfoxide. Proc Natl Acad Sci USA 68:378-82.
7. Gallarda, J. L., K. P. Foley, Z. Y. Yang, and J. D. Engel. 1989. The beta-globin stage selector element factor is erythroid-specific promoter/enhancer binding protein NF-E4. Genes Dev 3:1845-59.
8. Grigg, A. 2007. Effect of hydroxyurea on sperm count, motility and morphology in adult men with sickle cell or myeloproliferative disease. Intern Med J 37:190-2.
9. Humphries, R. K., G. Dover, N. S. Young, J. G. Moore, S. Charache, T. Ley, and A. W. Nienhuis. 1985. 5-Azacytidine acts directly on both erythroid precursors and progenitors to increase production of fetal hemoglobin. J Clin Invest 75:547-57.
10. Jiang, J., S. Best, S. Menzel, N. Silver, M. I. Lai, G. L. Surdulescu, T. D. Spector, and S. L. Thein. 2006. cMYB is involved in the regulation of fetal hemoglobin production in adults. Blood 108:1077-83.
11. Kinney, T. R., R. W. Helms, E. E. O'Branski, K. Ohene-Frempong, W. Wang, C. Daeschner, E. Vichinsky, R. Redding-Lallinger, B. Gee, O. S. Platt, and R. E. Ware. 1999. Safety of hydroxyurea in children with sickle cell anemia: results of the HUG-KIDS study, a phase I/II trial. Pediatric Hydroxyurea Group. Blood 94:1550-4.
12. Ley, T. J., and A. W. Nienhuis. 1985. Induction of hemoglobin F synthesis in patients with beta thalassemia. Annu Rev Med 36:485-98.
13. McCaffrey, P. G., D. A. Newsome, E. Fibach, M. Yoshida, and M. S. Su. 1997. Induction of gamma-globin by histone deacetylase inhibitors. Blood 90:2075-83.
14. McElveen, R. L., T. F. Lou, K. Reese, S. Xia, B. S. Baliga, and B. S. Pace. 2005. Erk pathway inhibitor U0126 induces gamma-globin expression in erythroid cells. Cell Mol Biol (Noisy-le-grand) 51:215-27.
15. Natta, C. L., G. A. Niazi, S. Ford, and A. Bank. 1974. Balanced globin chain synthesis in hereditary persistence of fetal hemoglobin. J Clin Invest 54:433-8.
16. Noguchi, C. T., G. P. Rodgers, G. Serjeant, and A. N. Schechter. 1988. Levels of fetal hemoglobin necessary for treatment of sickle cell disease. N Engl J Med 318:96-9.
17. Olivieri, N. F., and D. J. Weatherall. 1998. The therapeutic reactivation of fetal haemoglobin. Hum Mol Genet. 7:1655-8.
18. Orkin, S. H. 1992. GATA-binding transcription factors in hematopoietic cells. Blood 80:575-81.
19. Patrinos, G. P., and F. G. Grosveld. 2008. Pharmacogenomics and therapeutics of hemoglobinopathies. Hemoglobin 32:229-36.
20. Platt, O. S., D. J. Brambilla, W. F. Rosse, P. F. Milner, O. Castro, M. H. Steinberg, and P. P. Klug. 1994. Mortality in sickle cell disease. Life expectancy and risk factors for early death. N Engl J Med 330:1639-44.
21. Powars, D. R., J. N. Weiss, L. S. Chan, and W. A. Schroeder. 1984. Is there a threshold level of fetal hemoglobin that ameliorates morbidity in sickle cell anemia? Blood 63:921-6.
22. Raich, N., C. H. Clegg, J. Grofti, P. H. Romeo, and G. Stamatoyannopoulos. 1995. GATA1 and YY1 are developmental repressors of the human epsilon-globin gene. EMBO J 14:801-9.
23. Sankaran, V. G., T. F. Menne, J. Xu, T. E. Akie, G. Lettre, B. Van Handel, H. K. Mikkola, J. N. Hirschhorn, A. B. Cantor, and S. H. Orkin. 2008. Human fetal hemoglobin expression is regulated by the developmental stage-specific repressor BCL11A. Science 322:1839-42.
24. Schechter, A. N. 2008. Hemoglobin research and the origins of molecular medicine. Blood 112:3927-38.

25. Schmitt, J. M., G. A. Wayman, N. Nozaki, and T. R. Soderling. 2004. Calcium activation of ERK mediated by calmodulin kinase I. J Biol Chem 279:24064-72.
26. Scott, M. D., J. J. van den Berg, T. Repka, P. Rouyer-Fessard, R. P. Hebbel, Y. Beuzard, and B. H. Lubin. 1993. Effect of excess alpha-hemoglobin chains on cellular and membrane oxidation in model beta-thalassemic erythrocytes. J Clin Invest 91:1706-12.
27. Skarpidi, E., G. Vassilopoulos, Q. Li, and G. Stamatoyannopoulos. 2000. Novel in vitro assay for the detection of pharmacologic inducers of fetal hemoglobin. Blood 96:321-6.
28. Steinberg, M. H., Z. H. Lu, F. B. Barton, M. L. Terrin, S. Charache, and G. J. Dover. 1997. Fetal hemoglobin in sickle cell anemia: determinants of response to hydroxyurea. Multicenter Study of Hydroxyurea. Blood 89:1078-88.
29. Tanabe, O, D. McPhee, S. Kobayashi, Y. Shen, W. Brandt, X. Jiang, A. D. Campbell, Y. T. Chen, C. Chang, M. Yamamoto, K. Tanimoto, and J. D. Engel. 2007. Embryonic and fetal beta-globin gene repression by the orphan nuclear receptors, TR2 and TR4. EMBO J. 26:2295-306.
30. Tokumitsu, H., H. Inuzuka, Y. Ishikawa, M. Ikeda, I. Saji, and R. Kobayashi. 2002. STO-609, a specific inhibitor of the Ca(2+)/calmodulin-dependent protein kinase kinase. J Biol Chem 277:15813-8.
31. Witt, O., S. Monkemeyer, G. Ronndahl, B. Erdlenbruch, D. Reinhardt, K. Kanbach, and A. Pekrun. 2003. Induction of fetal hemoglobin expression by the histone deacetylase inhibitor apicidin. Blood 101:2001-7.
32. Zhou, W., D. R. Clouston, X. Wang, L. Cerruti, J. M. Cunningham, and S. M. Jane. 2000. Induction of human fetal globin gene expression by a novel erythroid factor, NF-E4. Mol Cell Biol 20:7662-72.

What is claimed is:

1. A method of treating β-thalassemia or sickle cell anemia comprising:

administering an effective amount of a pharmaceutical composition to a patient suffering from β-thalassemia, wherein the pharmaceutical composition comprising a compound of formula (I-a):

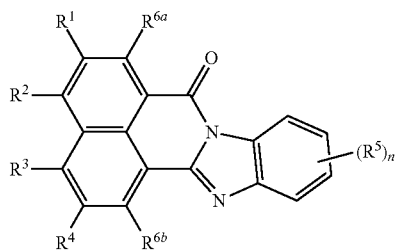

(I-a)

or a pharmaceutically acceptable salt, solvate, or hydrate thereof, wherein:

$R^1$, $R^2$, $R^3$, $R^4$, $R^{6a}$, and $R^{6b}$ are each independently selected from hydrogen, halogen, alkyl, alkenyl, alkynyl, heterocyclyl, aryl, —$OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$—$SO_2N(R^B)_2$, and —$NHSO_7R^B$;

each instance of $R^5$ is independently selected from hydrogen, halogen, alkyl, alkenyl, alkynyl, heterocyclyl, aryl, —$OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$—$SO_2N(R^B)_2$, and —$NHSO_2R^B$;

each $R^A$ is independently selected from hydrogen, alkyl, alkenyl, alkynyl, heterocyclyl, and aryl;

each $R^B$ is independently selected from hydrogen, alkyl, alkenyl, alkynyl, heterocyclyl, and aryl, or two $R^B$ taken together with the intervening nitrogen form a heterocycle;

n is 0, 1, 2, 3, or 4; and a pharmaceutically acceptable excipient.

2. The method according to claim 1, wherein the compound is of Formula (II):

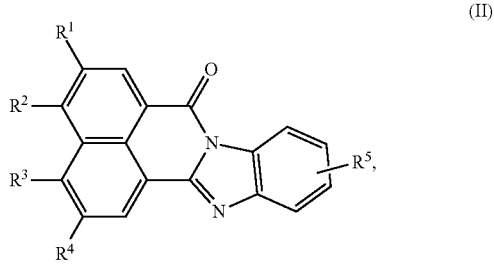

(II)

or a pharmaceutically acceptable salt, solvate, or hydrate thereof.

3. The method according to claim 2, wherein $R^1$, $R^2$, $R^3$, $R^4$, and $R^5$ are each independently selected from —H, —OH, —Cl, —Br, —F, $C_{1-6}$ alkyl, $C_{1-6}$ alkoxy, alkynyl, aryl, —$NO_2$, —$N(R^B)_2$, —$C(O)CH_3$, —$CO_2H$, —$C(O)OR^A$, —$C(O)N(R^B)_2$, —CN, heterocyclyl, —$SO_2$-alkyl, and —$SO_2$-aryl.

4. The method according to claim 2, wherein at least two of $R^1$, $R^2$, $R^3$, and $R^4$ are hydrogen.

5. The method according to claim 2, wherein at least two of $R^1$, $R^2$, $R^3$, and $R^4$ are hydrogen, and $R^5$ is hydrogen.

6. The method according to claim 2, wherein the compound is of Formula (III), (IV), or (V):

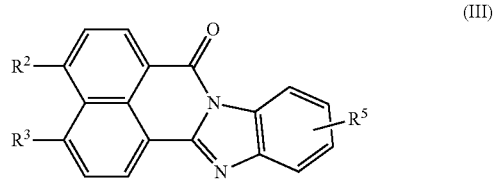

(III)

-continued

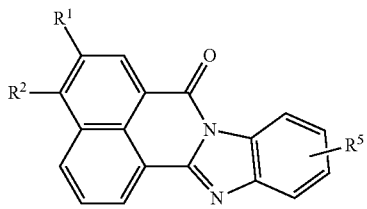
(IV)

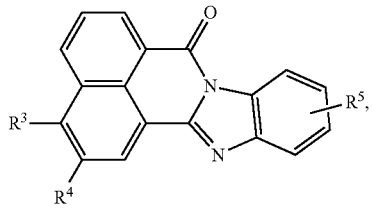
(V)

or a pharmaceutically acceptable salt, solvate, or hydrate thereof.

7. A pharmaceutical composition comprising a compound of formula (I-a):

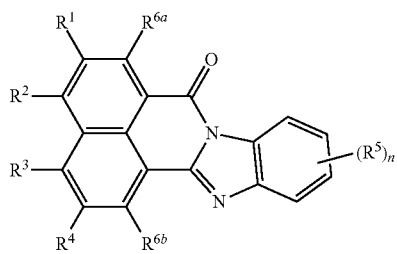
(I-a)

or a pharmaceutically acceptable salt, solvate, or hydrate thereof,
wherein:
$R^1$, $R^2$, $R^3$, $R^4$, $R^{6a}$, and $R^{6b}$ are each independently selected from hydrogen, halogen, alkyl, alkenyl, alkynyl, heterocyclyl, aryl, —$OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$—$SO_2N(R^B)_2$, and —$NHSO_2R^B$;
wherein one of $R^1$, $R^2$, $R^3$, and $R^4$ is of formula:

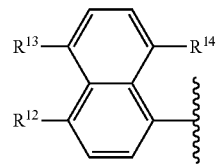

wherein $R^{12}$, $R^{13}$, and $R^{14}$ are each independently selected from hydrogen, halogen, alkyl, alkenyl, alkynyl, heterocyclyl, aryl, —$OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$; or $R^{12}$ and $R^{13}$ are taken together with their intervening atoms to form a carbocycle or heterocycle;
or $R^{12}$ and $R^{13}$ are taken together with their intervening atoms to form a carbocycle or heterocycle; and each instance of $R^5$ is independently selected from hydrogen, halogen, alkyl, alkenyl, alkynyl, heterocyclyl, aryl, —$OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$—$SO_2N(R^B)_2$, and —$NHSO_2R^B$;
each $R^A$ is independently selected from hydrogen, alkyl, alkenyl, alkynyl, heterocyclyl, and aryl;
each $R^B$ is independently selected from hydrogen, alkyl, alkenyl, alkynyl, heterocyclyl, and aryl, or two $R^B$ taken together with the intervening nitrogen form a heterocycle;
n is 0, 1, 2, 3, or 4; and
a pharmaceutically acceptable excipient.

8. The pharmaceutical composition according to claim 7, wherein $R^{12}$ and $R^{13}$ are each —$CO_2H$, or $R^{12}$, $R^{13}$, and $R^{14}$ are each —$CO_2H$.

9. The pharmaceutical composition according to claim 7, wherein one of $R^1$, $R^2$, $R^3$ and $R^4$ is of formula:

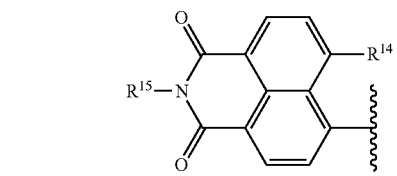

wherein $R^{14}$ is hydrogen, —$CO_2H$, —$C(O)OR^A$, —$C(O)N(R^B)_2$, —OH, —$NO_2$, —CN, halogen, alkyl, aryl, or heterocyclyl; and $R^{15}$ is selected from hydrogen, acyl, alkyl, aryl, and heterocyclyl.

10. The pharmaceutical composition according to claim 7, wherein compound is of formula (VI) or (VII):

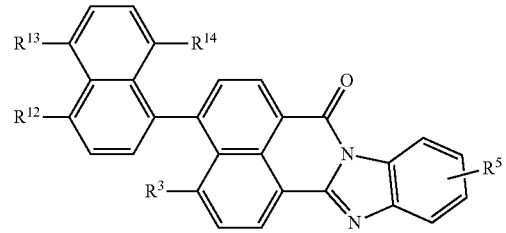
(VI)

(VII)

or a pharmaceutically acceptable salt, solvate, or hydrate thereof.

11. The pharmaceutical composition according to claim 10, wherein $R^1$, $R^3$, $R^5$, $R^{12}$, $R^{13}$, and $R^{14}$ are each independently selected from —H, —OH, —Cl, —Br, —F, $C_{1-6}$ alkyl, $C_{1-6}$ alkoxy, alkynyl, aryl, —$NO_2$, —$N(R^B)_2$, —$C(O)CH_3$, —$CO_2H$, —$C(O)OR^A$, —$C(O)N(R^B)_2$, —CN, heterocyclyl, —$SO_2$-alkyl, and —$SO_2$-aryl.

12. The pharmaceutical composition according to claim 10, wherein $R^1$, $R^3$, $R^5$, $R^{12}$, $R^{13}$, and $R^{14}$ are each independently selected from hydrogen, —CO$_2$H, —C(O)OR$^A$, —C(O)N(R$^B$)$_2$, —OH, —NO$_2$, —CN, halogen, alkyl, aryl and heterocyclyl.

13. The pharmaceutical composition according to claim 10, wherein R$^{12}$ and R$^{13}$ are taken together with their intervening atoms to form a carbocycle or heterocycle.

14. The pharmaceutical composition according to claim 13, wherein R$^{12}$ and R$^{13}$ are taken together with their intervening atoms to form a succinimidyl ring.

15. The pharmaceutical composition according to claim 10, wherein:
(i) R$^{12}$ and R$^{13}$ are each —CO$_2$H;
(ii) R$^{12}$, R$^{13}$, and R$^{14}$ are each —CO$_2$H;
(iii) R$^3$, R$^{12}$, R$^{13}$, and R$^{14}$ are each —CO$_2$H;
(iv) R$^1$, R$^{12}$, and R$^{13}$ are each —CO$_2$H; or
(v) R$^1$, R$^{12}$, R$^{13}$, and R$^{14}$ are each —CO$_2$H.

16. The method according to claim 1, wherein:
(i) R$^2$ is not —C(O)R$^A$;
(ii) R$^2$ is not —C(O)CH$_3$ or —NHCH$_2$CH$_2$OH;
(iii) R$^3$ is not —NH-allyl; or
(iv) R$^1$ and R$^4$ are not —NO$_2$.

17. The method according to claim 1, wherein when n is 2, each R$^5$ is not simultaneously methyl.

18. The method according to claim 1, wherein the compound is one of the following:

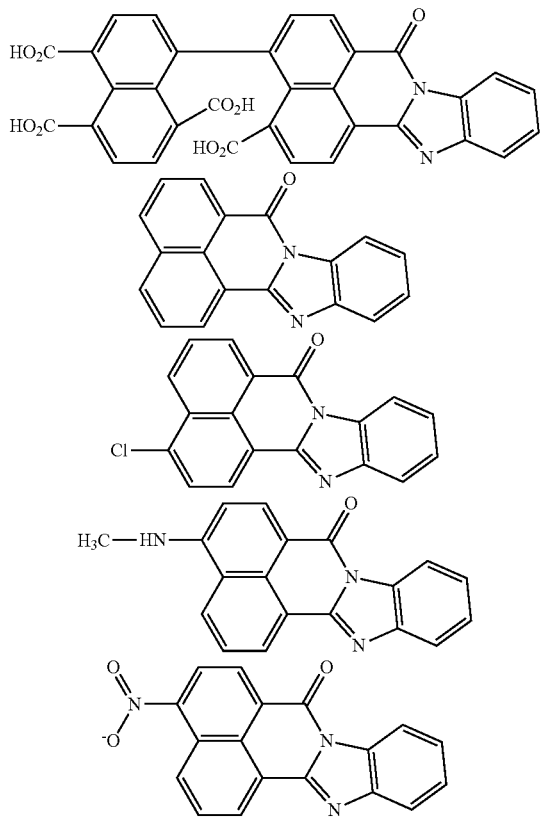

or a pharmaceutically acceptable salt, solvate, or hydrate thereof.

19. A method of inducing γ globin in vitro comprising:
contacting a cell with an effective amount of compound of formula (I-a):

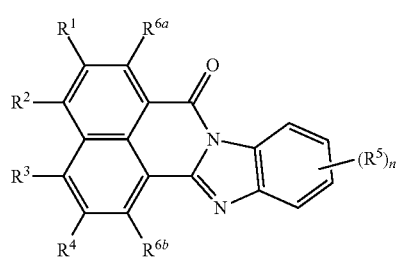

or a pharmaceutically acceptable salt thereof,
wherein:
R$^1$, R$^2$, R$^3$, R$^4$, R$^{6a}$, and R$^{6b}$ are each independently selected from hydrogen, halogen, alkyl, alkenyl, alkynyl, heterocyclyl, aryl, —OR$^A$, —OC(O)R$^A$, —SR$^A$, —N(R$^B$)$_2$, —N(R$^A$)C(O)R$^A$, —C(O)N(R$^B$)$_2$, —CN, —NO$_2$, —C(O)R$^A$, —C(O)OR$^A$, —S(O)R$^A$, —SO$_2$R$^A$, —SO$_2$N(R$^B$)$_2$, and —NHSO$_2$R$^B$;
each instance of R$^5$ is independently selected from hydrogen, halogen, alkyl, alkenyl, alkynyl, heterocyclyl, aryl, —OR$^A$, —OC(O)R$^A$, —SR$^A$, —N(R$^B$)$_2$, —N(R$^A$)C(O)R$^A$, —C(O)N(R$^B$)$_2$, —CN, —NO$_2$, —C(O)R$^A$, —C(O)OR$^A$, —S(O)R$^A$, —SO$_2$R$^A$, —SO$_2$N(R$^B$)$_2$, and —NHSO$_2$R$^B$;
each R$^A$ is independently selected from hydrogen, alkyl, alkenyl, alkynyl, heterocyclyl, and aryl;
each R$^B$ is independently selected from hydrogen, alkyl, alkenyl, alkynyl, heterocyclyl, and aryl, or two R$^B$ taken together with the intervening nitrogen form a heterocycle;
n is 0, 1, 2, 3, or 4.

20. A method of inducing gamma globin comprising: contacting a cell with an effective amount of compound of formula (I-a) of claim 7.

* * * * *

UNITED STATES PATENT AND TRADEMARK OFFICE
CERTIFICATE OF CORRECTION

PATENT NO.        : 8,822,491 B2
APPLICATION NO.   : 13/984687
DATED             : September 2, 2014
INVENTOR(S)       : Che-Kun James Shen et al.

It is certified that error appears in the above-identified patent and that said Letters Patent is hereby corrected as shown below:

In the Claims:

At Column 53, Claim 1, lines 51-52, please change "-$NO_2$, -$C(O)R^A$, -$C(O)OR^A$, -$S(O)R^A$, -$SO_2R^A$ -$SO_2N(R^B)_2$, and –$NHSO_7R^B$;" to "-$NO_2$, -$C(O)R^A$, -$C(O)OR^A$, -$S(O)R^A$, -$SO_2R^A$, -$SO_2N(R^B)_2$, and -$NHSO_2R^B$;"

At Column 53, Claim 1, line 57, please change "$OR^A$, -$S(O)R^A$, -$SO_2R^A$ -$SO_2N(R^B)_2$, and" to "$OR^A$, -$S(O)R^A$, -$SO_2R^A$, -$SO_2N(R^B)_2$, and"

At Column 55, Claim 7, lines 45-46, please change "-$NO_7$, -$C(O)R^A$, -$C(O)OR^A$, -$S(O)R^A$, -$SO_2R^A$ -$SO_2N(R^B)_2$, and –$NHSO_7R^B$;" to "-$NO_2$, -$C(O)R^A$, -$C(O)OR^A$, -$S(O)R^A$, -$SO_2R^A$, -$SO_2N(R^B)_2$, and -$NHSO_2R^B$;"

At Column 56, Claim 7, line 5, please change "$OR^A$, -$S(O)R^A$, -$SO_2R^A$ -$SO_2N(R^B)_2$, and" to "$OR^A$, -$S(O)R^A$, -$SO_2R^A$, -$SO_2N(R^B)_2$, and"

Signed and Sealed this
Second Day of December, 2014

Michelle K. Lee
*Deputy Director of the United States Patent and Trademark Office*